(12) United States Patent
Zander et al.

(10) Patent No.: US 8,231,590 B2
(45) Date of Patent: Jul. 31, 2012

(54) VISUALLY COORDINATED ABSORBENT PRODUCT

(75) Inventors: Teresa Marie Zander, Bonduel, WI (US); Kristi Jo Bryant, Appleton, WI (US); Debra A. Haase, Larsen, WI (US); Sheila Marie Heyrman, Appleton, WI (US); Kim Hoertsch, Neenah, WI (US); Adrienne Rae Loyd, Neenah, WI (US); William Grover Reeves, Appleton, WI (US); Garry Roland Woltman, Greenville, WI (US); Theodore T. Tower, Appleton, WI (US); Jennifer Pozniak, Menasha, WI (US); Angela Rae Heck, Appleton, WI (US); Richard Joseph Hantke, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1527 days.

(21) Appl. No.: 11/025,645

(22) Filed: Dec. 28, 2004

(65) Prior Publication Data

US 2005/0154365 A1 Jul. 14, 2005

Related U.S. Application Data

(63) Continuation-in-part of application No. 10/749,871, filed on Dec. 30, 2003.

(51) Int. Cl.
*A61F 13/15* (2006.01)
*B65D 73/00* (2006.01)
*A61L 15/00* (2006.01)

(52) U.S. Cl. ......... 604/385.01; 604/385.05; 604/385.02; 604/385.03; 206/494; 206/457; 206/458; 206/438

(58) Field of Classification Search ............. 604/385.01, 604/385.005, 385.02, 385.03, 385.05; 206/494, 206/457, 458, 438, 812
See application file for complete search history.

(56) References Cited

U.S. PATENT DOCUMENTS

| 3,635,221 A | 1/1972 | Champaigne, Jr. |
| 3,654,928 A | 4/1972 | Duchane |
| 3,665,923 A | 5/1972 | Champaigne, Jr. |
| 3,672,371 A | 6/1972 | Roeder |
| 3,683,919 A | 8/1972 | Ells |
| 3,688,771 A | 9/1972 | Werner |

(Continued)

FOREIGN PATENT DOCUMENTS

EP 0 841 049 A1 5/1998

(Continued)

OTHER PUBLICATIONS

Bailey, Robert W., *Human Performance Engineering*, Third Edition, published by Prentice Hall PTR, Upper Saddle River, New Jersey, 1996, pp. 52-61.

(Continued)

*Primary Examiner* — Jacqueline F. Stephens
(74) *Attorney, Agent, or Firm* — Randall W. Fieldhack

(57) ABSTRACT

A visually coordinated absorbent product includes a article component having a body side liner, a garment side outer cover and an absorbent core disposed between the body side liner and the garment side outer cover. The article component has at least a first and second visual characteristic, wherein the first visual characteristic is different than the second visual characteristic. The article component is disposed in a packaging component having at least the first and second visual characteristics. In one embodiment, the packaging component is an individual pouch sized and configured to hold a single, individual article component. In various embodiments, the visual characteristics can include color, embossment, printing, and/or side sealing.

2 Claims, 7 Drawing Sheets

U.S. PATENT DOCUMENTS

| | | | |
|---|---|---|---|
| 3,724,466 A | 4/1973 | Hendricks |
| 3,727,615 A | 4/1973 | Duchane |
| 3,769,979 A | 11/1973 | Freney |
| 3,838,695 A | 10/1974 | Comerford et al. |
| 3,856,014 A | 12/1974 | Yamauchi |
| 3,877,432 A | 4/1975 | Gellert |
| 3,881,490 A | 5/1975 | Whitehead et al. |
| 3,888,255 A | 6/1975 | Shah et al. |
| 3,897,783 A | 8/1975 | Ginocchio |
| 3,913,580 A | 10/1975 | Ginocchio |
| 3,927,674 A | 12/1975 | Schaar |
| 3,973,567 A | 8/1976 | Srinivasan et al. |
| 4,023,570 A | 5/1977 | Chinai et al. |
| 4,023,571 A | 5/1977 | Comerford et al. |
| 4,059,114 A | 11/1977 | Richards |
| 4,079,739 A | 3/1978 | Whitehead |
| 4,085,754 A | 4/1978 | Ness et al. |
| 4,157,410 A | 6/1979 | Mcclintock |
| 4,182,336 A | 1/1980 | Black |
| 4,186,743 A | 2/1980 | Steiger |
| 4,213,813 A | 7/1980 | Hendricks |
| 4,336,804 A | 6/1982 | Roeder |
| 4,337,772 A | 7/1982 | Roeder |
| 4,339,485 A | 7/1982 | Shibano et al. |
| 4,376,440 A | 3/1983 | Whitehead et al. |
| 4,380,450 A | 4/1983 | Reich |
| 4,402,689 A | 9/1983 | Baum |
| 4,545,372 A | 10/1985 | Lauritzen |
| 4,556,146 A | 12/1985 | Swanson et al. |
| 4,564,108 A | 1/1986 | Widlund et al. |
| 4,581,027 A | 4/1986 | Alvarado |
| 4,605,403 A | 8/1986 | Tucker |
| 4,648,513 A | 3/1987 | Newman |
| 4,675,013 A | 6/1987 | Ruffo |
| 4,678,465 A | 7/1987 | Avejic |
| 4,692,162 A | 9/1987 | Binker et al. |
| 4,735,316 A | 4/1988 | Froidh et al. |
| 4,765,477 A | 8/1988 | Froidh et al. |
| 4,781,712 A | 11/1988 | Barabino et al. |
| 4,801,494 A | 1/1989 | Datta et al. |
| 4,846,828 A | 7/1989 | Mendelsohn |
| 4,857,066 A | 8/1989 | Allison |
| 4,917,675 A | 4/1990 | Taylor et al. |
| 5,052,381 A | 10/1991 | Gilbert et al. |
| 5,074,293 A | 12/1991 | Lott et al. |
| 5,088,993 A | 2/1992 | Gaur |
| 5,141,505 A | 8/1992 | Barrett |
| 5,178,924 A | 1/1993 | Johnson et al. |
| 5,181,610 A | 1/1993 | Quick et al. |
| 5,295,988 A | 3/1994 | Muckenfuhs et al. |
| H1363 H | 10/1994 | Leeker |
| 5,358,499 A | 10/1994 | Seidy |
| 5,413,568 A | 5/1995 | Roach et al. |
| H1454 H | 6/1995 | Cucuzza et al. |
| 5,462,166 A | 10/1995 | Minton et al. |
| 5,474,818 A | 12/1995 | Ulrich et al. |
| 5,478,336 A | 12/1995 | Pigneul |
| 5,484,636 A | 1/1996 | Berg, Jr. et al. |
| 5,503,076 A | 4/1996 | Yeo |
| 5,520,676 A | 5/1996 | Lavash et al. |
| 5,527,578 A | 6/1996 | Mazurek et al. |
| 5,569,228 A | 10/1996 | Byrd et al. |
| 5,569,230 A | 10/1996 | Fisher et al. |
| 5,578,026 A | 11/1996 | Lavash et al. |
| 5,591,146 A | 1/1997 | Hasse |
| 5,591,147 A | 1/1997 | Couture-Dorschner et al. |
| 5,591,153 A | 1/1997 | Mattingly, III |
| 5,593,395 A | 1/1997 | Martz |
| 5,612,118 A | 3/1997 | Schleinz et al. |
| 5,669,899 A | 9/1997 | Osborn, III |
| 5,670,004 A | 9/1997 | Mattingly, III |
| 5,683,377 A | 11/1997 | Mizutani |
| 5,694,739 A | 12/1997 | Mattingly, III |
| 5,695,456 A | 12/1997 | Cartmell et al. |
| 5,730,739 A | 3/1998 | Lavash et al. |
| 5,769,837 A | 6/1998 | Parr |
| 5,792,131 A | 8/1998 | Mizutani |
| 5,827,251 A | 10/1998 | Moder et al. |
| 5,860,965 A | 1/1999 | Lavash et al. |
| 5,868,727 A | 2/1999 | Barr et al. |
| 5,873,871 A | 2/1999 | Lavash et al. |
| 5,954,201 A | 9/1999 | Finch et al. |
| 5,964,741 A | 10/1999 | Moder et al. |
| 5,986,165 A | 11/1999 | Moder et al. |
| 5,993,430 A | 11/1999 | Gossens et al. |
| 5,993,431 A | 11/1999 | Mcfall et al. |
| 6,010,001 A | 1/2000 | Osborn, III |
| 6,015,045 A | 1/2000 | Joseph et al. |
| 6,015,934 A | 1/2000 | Lee et al. |
| 6,024,732 A | 2/2000 | Samuelsson |
| 6,036,679 A | 3/2000 | Balzar et al. |
| 6,045,900 A | 4/2000 | Haffner et al. |
| 6,059,100 A | 5/2000 | Jones |
| 6,063,065 A | 5/2000 | Costa |
| 6,074,376 A | 6/2000 | Mills |
| 6,129,929 A | 10/2000 | Wick |
| 6,131,736 A | 10/2000 | Farris et al. |
| 6,140,551 A | 10/2000 | Niemeyer et al. |
| H1935 H | 1/2001 | Wilhoit et al. |
| 6,168,582 B1 | 1/2001 | Hasegawa |
| 6,183,587 B1 | 2/2001 | Mcfall et al. |
| 6,186,993 B1 | 2/2001 | Toyoshima et al. |
| 6,197,331 B1 | 3/2001 | Lerner et al. |
| 6,203,512 B1 | 3/2001 | Farris et al. |
| 6,231,715 B1 | 5/2001 | Schleinz et al. |
| 6,276,032 B1 | 8/2001 | Nortman et al. |
| 6,277,105 B1 | 8/2001 | Rynish |
| 6,293,932 B1 | 9/2001 | Balzar et al. |
| 6,299,607 B1 | 10/2001 | Osborn, III et al. |
| 6,312,417 B1 | 11/2001 | Hansson |
| 6,312,418 B1 | 11/2001 | Shimizu et al. |
| 6,315,765 B1 | 11/2001 | Datta et al. |
| 6,318,555 B1 | 11/2001 | Kuske et al. |
| 6,368,113 B1 | 4/2002 | Unger et al. |
| 6,380,455 B1 | 4/2002 | Moder et al. |
| 6,383,169 B1 | 5/2002 | Mills et al. |
| 6,387,084 B1 | 5/2002 | Vangompel et al. |
| 6,402,727 B1 | 6/2002 | Rosengrant |
| 6,454,748 B1 | 9/2002 | Ives |
| 6,461,343 B1 | 10/2002 | Schaefer et al. |
| 6,478,763 B1 | 11/2002 | Simonsen et al. |
| 6,497,692 B1 | 12/2002 | Tameishi et al. |
| 6,500,160 B2 | 12/2002 | Mizutani et al. |
| 6,502,695 B1 | 1/2003 | Kim et al. |
| 6,520,330 B1 | 2/2003 | Batra |
| 6,530,910 B1 | 3/2003 | Pomplun et al. |
| 6,544,242 B1 | 4/2003 | Kido et al. |
| 6,551,431 B2 | 4/2003 | Lee |
| 6,568,530 B2 | 5/2003 | Takahashi et al. |
| 6,569,136 B1 | 5/2003 | Tao et al. |
| 6,601,705 B2 | 8/2003 | Molina et al. |
| 6,601,706 B2 | 8/2003 | Mcmanus et al. |
| 6,681,934 B2 | 1/2004 | Kolterjohn et al. |
| 6,705,465 B2 | 3/2004 | Ling et al. |
| 6,716,203 B2 | 4/2004 | Sorebo et al. |
| 2002/0148749 A1 | 10/2002 | Briseboi et al. |
| 2003/0136529 A1 | 7/2003 | Burazin et al. |
| 2004/0015145 A1 | 1/2004 | Miura et al. |
| 2004/0186448 A1 | 9/2004 | Misek et al. |

FOREIGN PATENT DOCUMENTS

| | | |
|---|---|---|
| EP | 0 922 422 A1 | 8/1999 |
| EP | 1 138 293 A1 | 10/2001 |
| EP | 1 174 104 A1 | 1/2002 |
| EP | 1 213 001 A2 | 6/2002 |
| EP | 1 269 948 A2 | 1/2003 |
| EP | 1 300 125 A2 | 4/2003 |
| EP | 1 327 427 A1 | 7/2003 |
| EP | 1 357 046 A1 | 10/2003 |
| GB | 1 268 262 A | 3/1972 |
| JP | 02-001122 U | 1/1990 |
| JP | 03-015513 U | 2/1991 |
| JP | 03-054633 U | 5/1991 |
| JP | 04-083232 U | 7/1992 |
| JP | 04-099920 U | 8/1992 |
| JP | 04-131224 U | 12/1992 |
| JP | 05-005117 U | 1/1993 |

| | | | |
|---|---|---|---|
| JP | 06-011724 U | 2/1994 | |
| JP | 06-017725 U | 3/1994 | |
| JP | 06-142136 A | 5/1994 | |
| WO | WO 97/16143 A1 | 5/1997 | |
| WO | WO 99/32059 A1 | 7/1999 | |
| WO | WO 99/60965 A1 | 12/1999 | |
| WO | WO 00/13632 A1 | 3/2000 | |
| WO | WO 00/38915 A1 | 7/2000 | |
| WO | WO 00/44325 A1 | 8/2000 | |
| WO | WO 01/21126 A1 | 3/2001 | |
| WO | WO 01/95845 A1 | 12/2001 | |
| WO | WO 02/08087 A2 | 1/2002 | |
| WO | WO 02/30347 A1 | 4/2002 | |
| WO | WO 02/36443 A1 | 5/2002 | |
| WO | WO 02/057156 A1 | 7/2002 | |
| WO | WO 02/083047 A1 | 10/2002 | |
| WO | WO 02/096331 A2 | 12/2002 | |
| WO | WO 03/013406 A1 | 2/2003 | |
| WO | WO 03/013409 A1 | 2/2003 | |
| WO | WO 03/024706 A1 | 3/2003 | |
| WO | WO 03/053313 A2 | 7/2003 | |
| WO | WO 03/068123 A2 | 8/2003 | |
| WO | WO 2004/006818 A1 | 1/2004 | |

OTHER PUBLICATIONS

Bartlett, Neil R. et al., *Vision and Visual Perception*, Clarence H. Graham, editor, published by John Wiley & Sons, Inc., New York, 1965, second printing Oct. 1966, pp. 516-518.

Berthon, Pierre et al, "Understanding and Managing the Brand Space," *MIT Sloan Management Review*, Winter 2003, EBSCO Publishing, pp. 49-54.

Costa et al., *Shape Analysis and Classification: Theory and Practice*; Published by CRC Press, Boca Raton, FL, 2001.

Hunter et al., *The Measurement of Appearance*, Second Edition, Published by John Wiley & Sons, New York, 1987.

Schieber et al., "Optimizing Sensation and Perception in Older Adults", International Journal of Industrial Ergonomics, vol. 7, 1991 pp. 133-162.

Exhibit A—Digital color photograph of Stayfree® Maxipad and packaging available from Johnson & Johnson prior to Dec. 30, 2003.

Exhibit B—Digital color photograph of Kotex® pad with peel strip available from Kimberly-Clark Corp. prior to Dec. 30, 2003.

Exhibit C—Digital color photograph of Kotex® pad available from Kimberly-Clark Corp. prior to Dec. 30, 2003.

Exhibit D—Digital color photograph of Whisper packaging and absorbent pad distributed in Korea, Japan and Hong Kong by Procter & Gamble prior to Dec. 30, 2003, and as early as Jul. 2003.

Exhibit E—Digital color photograph of Whisper pad and wrap distributed in Korea, Japan and Hong Kong by Procter & Gamble prior to Dec. 30, 2003, and as early as Jul. 2003.

Exhibit F—Digital color photograph of packaging and absorbent pad distributed in Korea by Kimberly-Clark Corp. prior to Dec. 30, 2003, and as early as Jan. 2001.

Exhibit G—Digital color photograph of packaging and absorbent pad distributed in Korea by Kimberly-Clark Corp. prior to Dec. 30, 2003, and as early as Jan. 2001.

US 5,699,911, 12/1997, Joseph et al. (withdrawn)

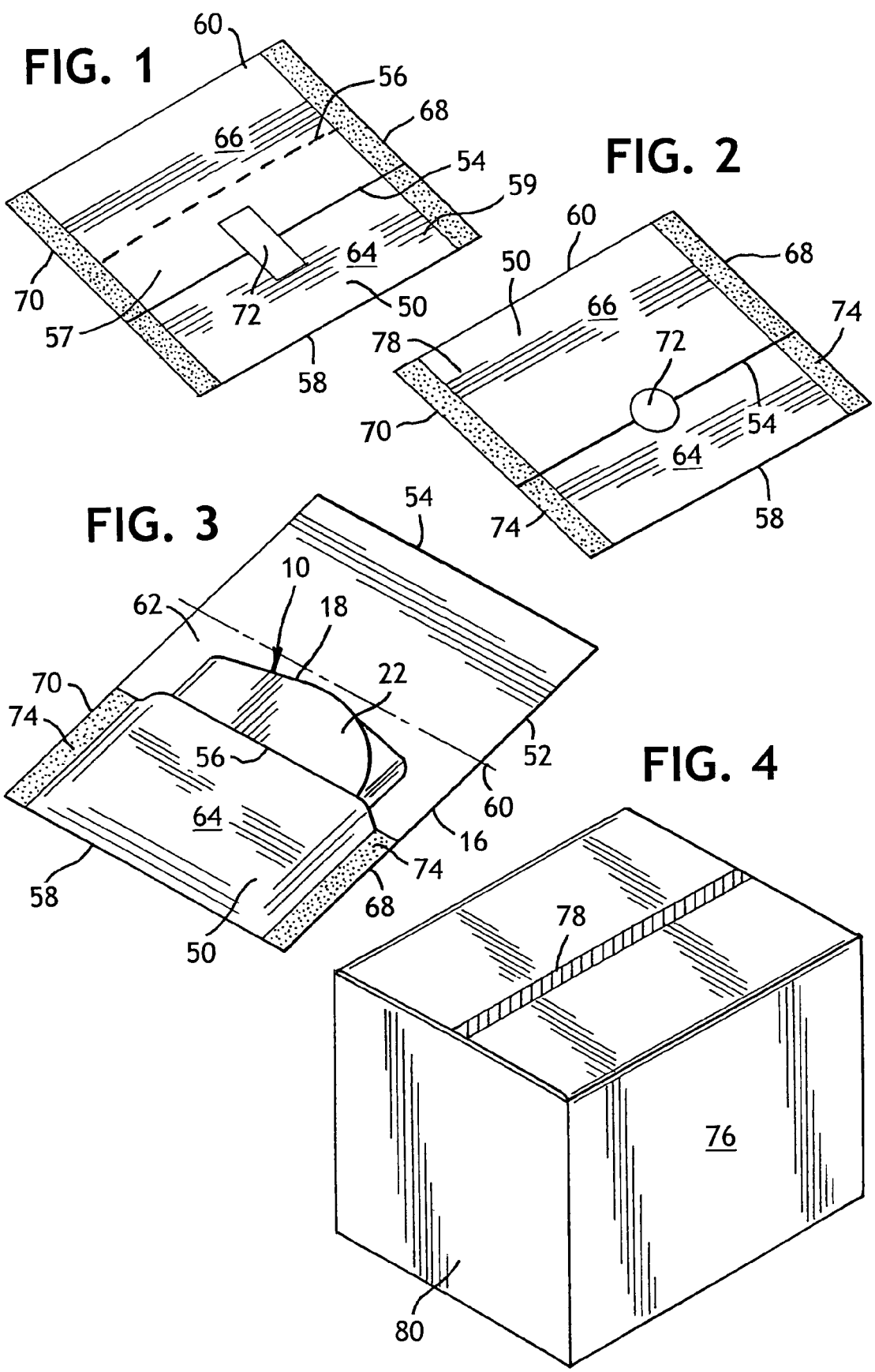

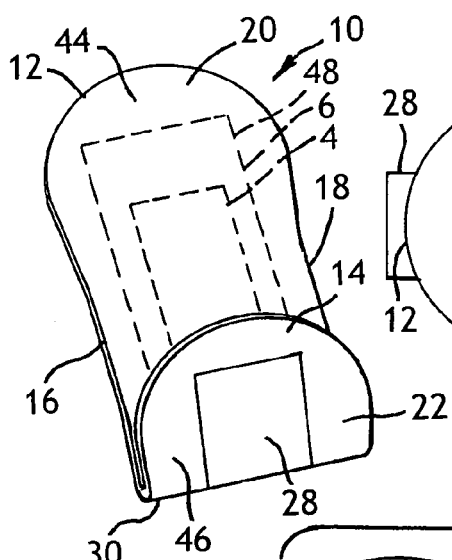
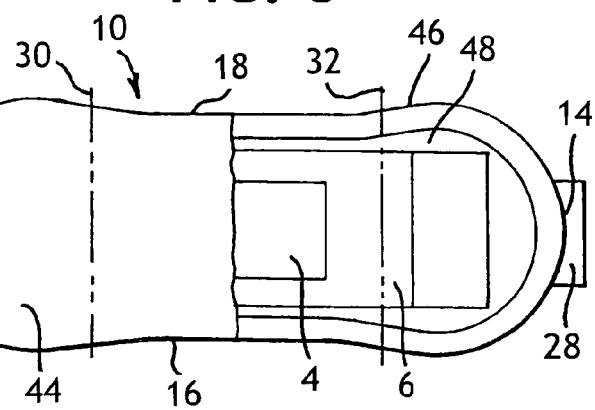
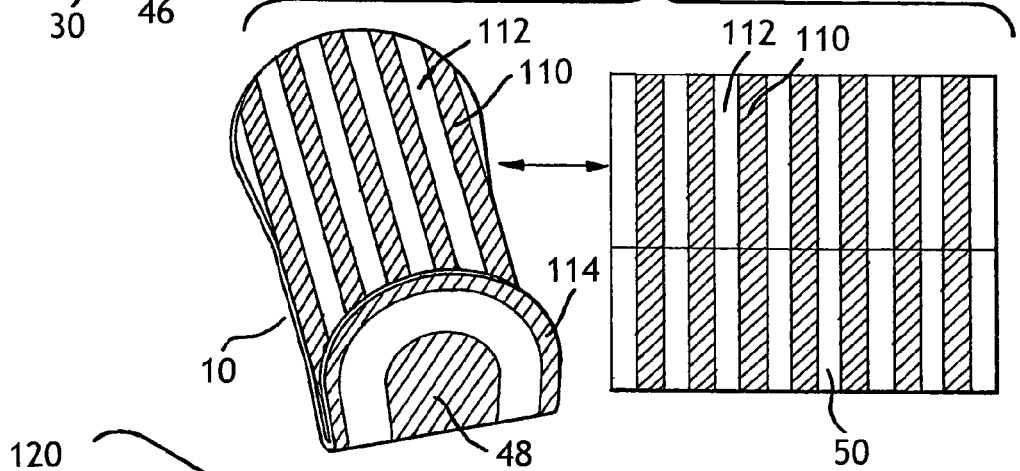
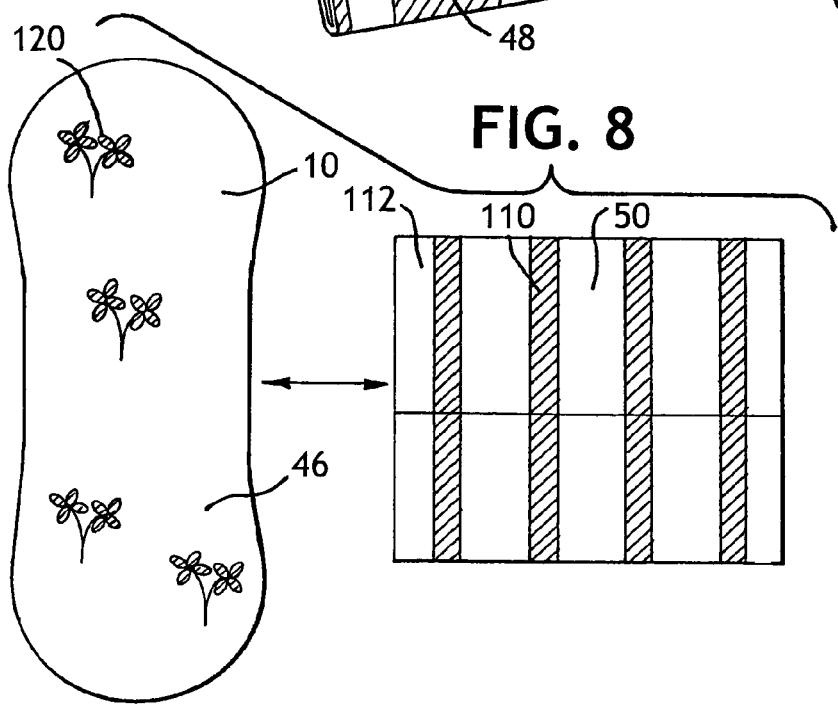

VISUALLY COORDINATED ABSORBENT PRODUCT

This application is a continuation-in-part of U.S. patent application Ser. No. 10/749,871, filed Dec. 30, 2003, and claims the benefit of the filing date of U.S. patent application Ser. No. 10/749,871.

FIELD OF THE INVENTION

The present invention relates generally to absorbent products, and in particular, to visually coordinated absorbent products.

BACKGROUND OF THE INVENTION

Disposable absorbent articles have become an integral part of the lives of many people. These disposable absorbent articles contribute to life experiences including shopping experiences and experiences in restrooms, especially public restrooms. Often these articles contribute to these experiences in a negative manner. This negative contribution often begins with the article appearance. Basing an opinion of an article on first impression may be unfair, but it is often the norm. From the time a consumer see the article first advertised to the time that the consumer disposes of the article, the consumer is generating an opinion about the article that can be very different from that which is desired by the manufacture, solely based on the appearance of the disposable absorbent article.

Typically, the appearance of many disposable absorbent articles includes a mixture of uncoordinated solid colors that typically give the disposable absorbent article a sanitary appearance, which is easily recognized as an absorbent article. For example, a typical appearance for an incontinent article consists of combination of a solid white and may be some other solid non-white color such as blue, pink, green, or yellow. When a non-white color is used, it often contrasts with the white color. The contrast is provided to draw attention to some attribute of the articles function, such as absorbency. The appearance of a solid blue or green within the pad has been used by companies to denote added absorbency. Solid pink and yellow have been used but have a negative connotation reminding the user that they have a problem due to the association of these colors with bodily fluids like menses and urine. The use of these combinations of solid colors generally conveys a message to a consumer of these absorbent articles that the consumer has a problem. Often, this impression is reinforced by advertising and use. One of the last things that a consumer wants to have is the appearance of the article that advertises to others or reminds them that they have a problem. Accordingly, a need remains for a disposable absorbent article that gives an impression of being more than an absorbent but it is an essential component of a consumers clothing ensemble.

Typically, absorbent articles such as pads or pantiliners include one or more elements, such as an outer cover, an absorbent core, a body side liner and peel strip. Such articles are often individually wrapped in a pouch or similar wrapper, or are wrapped as a group of articles. A plurality of articles, whether or not individually wrapped, is also typically sold in bulk packaging, such as a bag or box. Often, the various elements of the article, the individual pouch and the bulk packaging are individually designed without any effort to coordinate their appearance or aesthetics of the various components. For example, a typical incontinence pad may be solid white or white with pink or blue stripes on the body side surface and may have a peel strip with a print that is pink or blue. The pad is wrapped in a solid white or solid pink pouch, with the plurality of pouches packaged in a bag perhaps having some blue or pink coloration. In this way, while some colors (e.g., white and pink or blue) are used on each of the components, they do not coordinated between the article and individual wrapper and/or bulk packaging. As such, the consumer is not made confident that the overall product, including the pad, the pouch and/or the packaging, was designed together. Accordingly, a need remains for an absorbent article that is visually coordinated with itself or with its packaging so as to invoke an impression from the user that the individual components, i.e., the absorbent article and the packaging component, of the absorbent product were designed together and are of a high quality.

In addition, a consumer may not want others to know that they are carrying an absorbent article. A consumer may want the article to be masked or hidden or otherwise disguised. Current pouches achieve this masking by using a relatively heavy, uniform-micro embossed, uniform-colored film material which can prevent an observer from discerning what is contained in the pouch. Such materials can be relatively expensive. Lighter weight materials, however, are typically more see-through, thereby allowing observers to discern the contents of the pouch. Current pouches also appear rectangular in shape containing linear lines. The combination of the material and construction can give the wrapped article an appearance easily recognized by others as an absorbent article. Accordingly, a need remains in the art for an absorbent article that is visually coordinated with itself and/or with its packaging, and which is not discernable through relatively see-through packaging and rectangular construction of the packaging.

In the case of feminine personal care articles, such as sanitary napkins and the like, there is a need for absorbent article which can provide a possible emotional benefit to the user. The menstrual period is often an inconvenience at best or disabling at worst. Many women experience both physical and emotional discomfort during the menstrual period. This discomfort can be exasperated by others discovering that a user of the feminine care articles is in fact using feminine personal care articles at a given time. This is especially a problem in for young women and particularly teenagers. Generally, sanitary napkins available on the market meet the physical needs, e.g. absorbency, but provide little, if any, emotional support for the user during a time of emotional need. Typical sanitary napkins available on the market have a white color or a simple combination of colors to provide a sanitary appearance. As a result, the user of the sanitary napkins is provided with essentially no emotional benefit by the appearance of the sanitary napkin; In a similar manner, incontinence may also cause a downturn in the emotional state of the incontinent person. Therefore, there is a need in the art to provide a possible emotional benefit to the users of feminine personal care articles and incontinence articles.

In addition, many women prefer that items in their lives blend in or fit into their lives. As a result, many items in a woman's life are coordinated and/or are matched. Many items in a woman's life have a feminine flair. One item used in lives of women which is not matched or coordinated is personal care articles, including sanitary napkins and incontinence pads. Personal care articles are generally white in color or have a simple combination of colors, such as white and one additional color. Available personal care products are generally not coordinated and often appear to be masculine.

Therefore, there is a need for coordinated personal care products or personal care products having an overall feminine flair.

SUMMARY OF THE INVENTION

Briefly stated, in one aspect of the present invention, the present invention provides a visually coordinated absorbent product comprising at least a first element and a second element. Each element has at least a first and second visual characteristic, wherein the first and second visual characteristics are different from each other and the first and second visual characteristic of the first element are matched to the first and second visual characteristics of the second element. In an addition aspect, there are at least three visual characteristics that are matched.

In another aspect of the present invention, provided is a visually coordinated absorbent product having at least a first element, a second element and a third element, wherein the first element has at least a first and second visual characteristic, the second element has at least one visual characteristic which is matched to the first visual characteristic of the first element and the third element has at least one visual characteristic which is matched to the second visual characteristic of the first element. The first element causes the second and third elements to be matched.

In another aspect of the present invention, provided is a visually coordinated absorbent product. The absorbent product has an absorbent article component with a garment side outer cover and an absorbent core adjacent the garment side outer cover. Also the article component has at least a first and second visual characteristic, wherein said first visual characteristic is different than said second visual characteristic. In addition to the absorbent article, the product also has a packaging component having at least a first and second visual characteristic. The first and second visual characteristics of the absorbent article are coordinated to the first and second visual characteristics of the packaging component and wherein said article component is disposed in said packaging component. There may be more that two visual characteristics that are coordinated. For example, there may be three, four, five, six, seven, eight, nine or more visual characteristic that are coordinated. In various embodiments, the visual characteristics can be generated by color, embossment, printing, and/or side sealing.

In another aspect of the present invention, provided is a visually coordinated absorbent product having an absorbent article, a first packaging component and a second packaging component. The absorbent article component has a body side liner, a garment side outer cover and an absorbent core disposed between said body side liner and said garment side outer cover. The first packaging component has at least first and second visual characteristics, and the absorbent article component is disposed in said first packaging component. The second packaging component having said at least said first and second visual characteristics, and the first packaging component is disposed in said second packaging component.

In another aspect, the present invention provides a visually coordinated absorbent product having an absorbent article component and a packaging component. The absorbent article component has a garment side outer cover and an absorbent core adjacent the garment side outer cover. In addition, the article component has at least a first and second visual characteristic, wherein said first visual characteristic is different than said second visual characteristic. The packaging component is transparent or translucent and the a first and second visual characteristics of the absorbent article are visible thru the packaging components such that the packaging component appears to have the a first and second visual characteristics on the surface thereof.

In a further aspect of the present invention, provided is a visually coordinated absorbent product having at least a first element and a second element, each element has at least a first and second visual characteristic. The first and second visual characteristics are different from each other and the first and second visual characteristic of the first element are coordinated to the first and second visual characteristics of the second element.

The various aspects provide significant advantages over other absorbent products. For example and without limitation, the user is provided with an impression that the product is of high quality, and that the product and wrapper were designed together, rather than piece meal. In addition, the visually coordinated product and wrapper may provide the user with an emotional benefit, allowing them to feel more feminine with respect to female absorbent products, and to feel better about the product they are using. The visual characteristics can also identify the product for the user, for example provide source identification. In other aspects, the coordination of the elements of the absorbent products, or the coordination of the absorbent product with the wrapper, allows the manufacturer to use a relatively see-through packaging material without sacrificing the ability to hide the contents of the packaging. For example, a relatively light basis weight non-woven material can be used for the packaging, thereby reducing the overall costs of the product.

The present invention provides for personal care products which may provide an emotional benefit to the user in a time of need. In this aspect, the absorbent products and the wrappers for the absorbent products are match or coordinated and may be provided with a feminine flair, through the use of colors, patterns, aromas and tactile properties, thereby providing a more positive product use experience.

This invention is an absorbent product this is visually coordinated to a consumer. A product will be visually coordinated when one or more elements of the product have two or more visual characteristics that are either matched or are caused to match. These visual characteristics may be visible patterns of color on the elements of the product. The color of these patterns can be described by the value of the hue, saturation, and luminosity. This color will be determined from the visible spectral and angular distribution of light coming from an object. The patterns can be described by their location, extent, shape, and orientation. These patterns may have smaller patterns contained within them. The pattern may be the result of the non-uniform chemical composition of the element like the printing of a pattern of a dye or from the texture of the element like the embossing of a pattern. The pattern will be determined from the visible spatial, spectral and angular distribution of light coming from an object.

Although any element could be involved the coordination, preferable one element would be part of each separable element of the product like one element of the absorbent article and another element would be part of the packaging. When the packaging consists of more than one separable element, an element of each separable element of the packaging would be involved like the wrapper and the bag. When the article consists of more than one separable element, an element of each separable element of the article would be involved like the pad and peel strip. These configuration ties together those separable elements of the product.

Although any visual characteristic could be involved in the coordination, desirably the visual characteristic provides an emotional benefit to a consumer. The characteristic is recognized by the consumer in a positive emotional sense. When the consumer is a female, a characteristic that has a feminine flair like a flower pattern or a pink color would be preferable. The characteristic that has a discretionary value like a camouflage pattern or a dark color may be desirable.

Although any visual characteristic could be involved in the coordination, desirably the visual characteristic is reinforced by sensory characteristics like tactile and aromatic. When visual characteristic communicates a feminine flair, the tactile characteristics would preferable communicate comfort like a silky feel.

BRIEF DESCRIPTION OF THE DRAWINGS

FIG. 1 is perspective view of a first embodiment of an individual wrapper component.

FIG. 2 is a perspective view of a second embodiment of an individual wrapper component.

FIG. 3 is a perspective view of an individual packaging component in an open configuration with an absorbent product component in a partially unfolded configuration.

FIG. 4 is a perspective view of an outer packaging component configured to hold a plurality of product components.

FIG. 5 is a perspective view of a product component in a partially folded configuration.

FIG. 6 is a body-side plan view of an exemplary product component with portion thereof partially cut away.

FIG. 7 is a perspective view of one embodiment of a product component with a wrapper component.

FIG. 8 is a perspective view of another embodiment of a product component with a wrapper component.

DEFINITIONS

Figure 9:
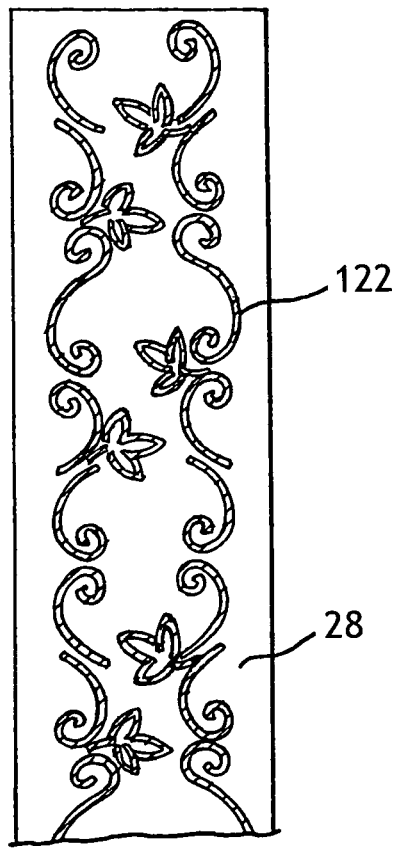
FIG. 9 is one embodiment of a peel strip having a pattern thereon.

It should be noted that, when employed in the present disclosure and claims, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "article" or "article component" is used to describe an item which is to be used by a consumer. For example, absorbent articles include without limitation diapers, pull-up type training pant garments, adult incontinence garments, male incontinence products, tampons, vaginal suppositories, pantiliners, female incontinence pads, and sanitary napkins, which are sometime referred to as "personal care articles" or "absorbent personal care articles". Examples of commercially available personal care articles include, without limitation, Poise® adult care products, including pantiliners and pads, and Kotex® feminine care products, including pads, tampons and liners, Depend® undergarments, underwear and guards, all available from Kimberly-Clark Corporation, Neenah, Wis. Various exemplary products are disclosed in U.S. Pat. No. 6,315,765, entitled "Elasticized Absorbent Pad," and U.S. patent application Ser. No. 10/392,116, filed Mar. 19, 2003 and entitled "Multilayer Absorbent Article", the entire disclosures of which are hereby incorporated herein by reference. For the purposes of this patent, a separate or individual peel strip which protects the adhesive is considered to be a part of the article. If the peel strip also serves as a wrapper, then the peel strip/wrapper is considered as a packaging component.

As used herein, the term "packaging" or "packaging component" is used to describe any items which are associated with the article, but not used within the absorbency purpose of the article. Packaging can be any items which are used to transport, store, protect or hide the article. Examples of packaging include, without limitation, wrappers, pouches, bags, boxes and the like. Typically, boxes or bags are placed on store shelves. Generally, these boxes or bags contain a plurality of absorbent personal care articles. These items may be referred to as an "outer packaging component". In addition, packaging may include an inner wrapper or pouch in which the one or more absorbent personal care articles are placed. Wrappers and pouches may be referred to as an "inner packaging component". These wrapper or pouches can be placed into a second packaging component, such as the outer packaging described above.

As used herein, the term "product" is used to describe the items sold or otherwise, provided to a consumer or user. A product includes an article component and a packaging component.

As used herein, the term "element" is used to describe a separate or individual component of a product or packaging. Product elements may include, for example, a liner, an absorbent core, an outer cover, an attachment system, etc. Packaging elements may include, wrapper materials, pouch materials, bag materials, bag handles, wrappers, pouches, bags and the like.

As used herein, the term "visual characteristic" is intended to mean a visible, distinguishing or recognizable feature or attribute of a visible aspect of one or more elements of the product. Visual characteristics-include color, texture, pattern, form and the like.

As used herein, the term "visible" is intended to mean attribute of feature which is visually perceived by an individual user or consumer. Generally for a consumer or user, the attribute should be visible in the range of about 0.25 feet (0.075 meters) to about 3 feet (0.91 meters). For a non-consumer or non-user, generally for an attribute to be visible, the distance should be greater than about 3 feet (0.91 meters). As used herein, "perceived" or "perception" is the ability to recognize an attribute or feature when the visual angle that the attribute or feature subtends is greater than about 5 minutes of visual arc and less than about 45 minutes of visual arc as determined by the following equation:

$$\text{Minutes of visual arc} = 3438 * (\text{length of the object} / \text{distance from object})$$

Where

Length of the object=size of the object measured perpendicular to the line of sight Distance from object=distance from the front of the eye to the object along the line of sight A minute of visual arc is $1/60^{th}$ of 1 degree.

As used herein, the term "color" is intended to mean an individual's perception of the spectral composition of visible light coming from a portion of an object. Color characteristics include hue, saturation and luminosity. Each is a separate color characteristic. Hue is the attribute of a color which allows it to be classified as a given color. Saturation, which is sometimes referred to as vividness, is the intensity of the color. Saturation is the degree of freedom from gray. Luminosity, sometimes referred to as value, is the degree of lightness (paleness) or darkness in a color. For example, a blue with white added is a pale color, e.g. baby blue and blue with black added is a dark color, e.g. navy blue. A measurement of hue, saturation and luminosity are described in more detail below.

As used herein, the term "form" is used to describe an individual's perception of the spatial variation of visible light due to the bulk shape and structure of a portion of an object in three dimensions. Stated another way, form is shape and structure of an item which distinguishes it from its surrounding which causes a spatially discontinuous change in light that is transmitted through or reflected from an item.

As used herein, the term "texture" is used to describe the individual's perception of the spatial variation of visible light due to surface structure of a portion of an object in two dimensions. Textures can be visual effects generated by surface roughness and visual illusion created by mere color or pattern. Texture may be the result of the natural characteristics of a given material as a result of the material formation process. Textures may also be imparted to a material using techniques known to those skilled in the art including, for example, printing, embossing, bonding, aperturing and the like.

As used herein, the term "pattern" is used to describe the individual's perception of spatial variation of visible light due to contrasts in spatial variation of light due to the color, form, and texture of a portion of an object incorporated into the object by the manufactory of the elements. This contrast creates various visual distinct regions or lines sometimes referred to as "figures" within its surrounding sometimes referred to as "ground." Patterns can be formed by combinations of contrasting color, form, and texture relative to its surroundings. An element can have more than one pattern, but each pattern would be distinguishable, recognizable, and separate from the other patterns on the element. Pattern is also a term used to describe the observer's perception of combined effect of more than one color, form, or texture within a portion of an observer's field of view. Patterns may have a "length", "extent", "shape", "position" and "orientation". Each is a pattern characteristic within the scope of the present invention. Length is the perceived distance along the major axis of the pattern. The "major axis" is the axis of the longest symmetry. The extent of the pattern is the area of the pattern. Shape is simply the shape of the pattern. Position is the location of the pattern relative to its surroundings. And orientation is position of the major axis of the pattern relative to its surroundings.

As used herein, the term "match" or "matched" is used to describe the way or degree two items visually fit together or are caused to fit together. For example, two items are considered matched if some aspects of one of the items are identical to similar aspects of another item. In one form of match, two items resemble each other are said to match.

As used herein, the term "coordinate" or "coordination" is used to describe how two components or elements of the overall personal care product visually belong together. Visual characteristics are said to coordinate if one aspect of the visual characteristic is the same or falls within limits described with this specification. Components or elements are considered to be coordinated if they match, or are caused to match. Colors may be coordinated if they have a hue, luminosity or saturation that match within limits described below.

As used herein, the term "caused to match" is used to describe how two components are made to appear matched one another by using a coordinating feature on an element of one or more of the components which has visual characteristic which tie two other elements together. For example, if two elements of an personal care product each have a visual characteristic which are different and a third element has visual characteristics which match each of the visual characteristics of the two elements, the third element causes the two elements to be matched to one another.

As used herein, the term "nonwoven fabric or web" means a web having a structure of individual fibers or threads which are interlaid, but not in a regular or identifiable manner as in a knitted or woven fabric. The term also includes individual filaments and strands, yarns or tows as well as foams and films that have been fibrillated, apertured, or otherwise treated to impart fabric-like properties. Nonwoven fabrics or webs have been formed from many processes such as for example, melt-blowing processes, spunbonding processes, airlaying processes and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic, syndiotactic and random symmetries.

The term "body side" should not be interpreted to mean in contact with the body of the user, but rather simply means the side that would face toward the body of the user, regardless of whether an undergarment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the undergarment is actually being worn by a user, regardless of whether any such outer garments are actually worn and regardless of whether there may be intervening layers between the component and any outer garment.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected by the end user, during the normal operation and use of the absorbent garment. Moreover, the separation of two elements being so connected is likely to damage or make unusable at least one of the two elements.

The terms "connecting," "coupled," "attached," and "secured," and variations thereof, broadly covers two or more items being directly connected one to the other, or by way of one or more intervening members or components.

DETAILED DESCRIPTION OF THE INVENTION

The present invention provides a visually coordinated disposable absorbent product; The disposable absorbent product has at least two elements which have at least one visual characteristic in common with the other element. In one aspect of the present invention, provided is a visually coordinated absorbent product having at least a first element and a second element. Each element has at least a first and second visual characteristic, wherein the first and second visual characteristics are different from each other. In addition, the first and second visual characteristic of the first element are matched to the first and second visual characteristics of the second element. More than two elements may have visual characteristic that are matched and there may also be more than two visual characteristics which may be matched. In another aspect of the present invention, provided is a visually coordinated absorbent product having at least a first element, a second element and a third element. The first element has at least a first and second visual characteristic, the second element has at least one visual characteristic which is matched to the first visual characteristic of the first element and the third element has at least one visual characteristic which is matched to the second visual characteristic of the first element. By having the first element with a visual characteristic of the other elements, the first element causes the second and third elements to be matched. It is noted that more than three elements may be caused to match. Each element may have more than one matched visual characteristic.

In another aspect of the present invention, generally a visually coordinated disposable absorbent product has an absorbent article component and a packaging component. At least one element of each of the components are matched or caused to be matched to at least one element of the other component, or in the aspect of color, have a hue, luminosity or saturation within limits described below. It has been discovered that providing a coordinated absorbent article and packing component, many advantages may be obtained, including cost saving for the pouch material, improved discretion for the users of the absorbent articles since the coordination tends to camouflage the absorbent articles in packaging components.

In addition, the present invention provides for products with a theme, such as femininity, which are more aesthetically pleasing to a user and which may provide for an emotional benefit to the user. The article component has at least a first and second visual characteristic, wherein the first visual characteristic is different than the second visual characteristic. The article component is disposed in a packaging component having at least the first and second visual characteristics.

Disposable absorbent articles such as, for example, feminine care and incontinent absorbent articles, generally include a liquid pervious topsheet, a substantially liquid impervious backsheet, and an absorbent core positioned and held between the topsheet and the backsheet. The topsheet is generally operatively permeable to the liquids that are intended to be held or stored by the absorbent article, and the backsheet may be substantially impermeable or otherwise operatively impermeable to the liquids intended to be held or stored. Disposable absorbent articles may also include other optional components or layers, such as liquid wicking layers, liquid distribution layers, barrier layers, and the like, as well as combinations thereof, which may improve the fluid handling and storage properties of the disposable absorbent article. Generally, disposable absorbent articles and the components thereof provide a body-facing surface and a garment-facing surface. As an alternative, the substantially liquid impervious backsheet may be replaced with a liquid pervious backsheet. When a liquid pervious backsheet is used, generally the absorbent personal care article may be used in conjunction with another liquid impervious layer or article, such as liquid impervious pants.

To obtain a better understanding of the absorbent articles of the present invention, which may be present in a wrapper component as the packaging component, attention is directed to FIGS. 5 and 6. In FIGS. 5 and 6, an exemplary absorbent article 10 is shown as including an outer cover 46 (otherwise referred to as a baffle or backsheet), an absorbent core 48, an optional tissue layer 6, an optional surge layer or optional distribution layer 4 and a body side liner 44 (also referred to as the top sheet). The absorbent article 10 also has a first side 16 and a second side 18. The first and second sides 16, 18, respectively, are the longitudinal sides of the elongated absorbent article. The sides can be contoured, for example in a concave shape, or they can be linear. The sides can further include flaps (not shown) that extend laterally outward. Flaps are known in the art are shown in, for example U.S. Pat. No. 6,387,084 issued to VanGompel et al., which is hereby incorporated by reference in its entirety. In one embodiment (not shown), one or more elastic elements are disposed along the sides to form a gasket with the body of the user. Elastic sides are known in the art, as is shown in U.S. Pat. No. 6,315,765 issued to Datta et al., which is hereby incorporated by reference in its entirety. In one embodiment, the elastic elements are disposed between the body side liner and the outer cover.

The absorbent article 10 has a first body facing surface 20, which usually includes the outer surface of the body side liner 44, and a second garment facing side surface 22, which usually contains an outer portion of the outer cover 46. Applied to at least a portion of the second garment side surface 22 is a garment attachment adhesive. In various embodiments, the garment attachment adhesive is configured as a single band of adhesive or as two or more spaced apart strips. Alternatively, the garment attachment adhesive includes a swirl pattern of adhesive which encompasses a major portion of the second garment facing surface 22 of the absorbent article 10.

A release strip 28, also known as a releasable peel strip, is removably secured to the garment attachment adhesive and serves to prevent premature contamination of the adhesive before the absorbent article 10 is secured to the crotch portion of an undergarment. In various embodiments, the garment attachment adhesive is designed to be secured to the inner crotch portion of an undergarment so as to keep the absorbent article in register with the body of the user. The release strip 28 may extend beyond one or both of the ends 12, 14 of the outer cover, as shown in FIG. 6. As an alternative, the release strip may be shorter than the ends of the outer cover 12 and 14, as shown in FIG. 5. Generally, the only requirement for the length of the release strip 28 is that the release strip covers the garment adhesive often present on the outer cover 46.

The body side liner or topsheet 44, which is preferably liquid permeable, may be formed from one or more materials.

The body side liner or topsheet 44 must be able to manage different body excretions depending on the type of article. In feminine care articles, often the body side liner or body contacting layer must be able to handle menses and urine. In the present invention, the body side liner or topsheet 44 may include a layer constructed of any operative material, and may be a composite material. For example, the liner or body contacting layer can include a woven fabric, a nonwoven fabric, a polymer film, a film-nonwoven fabric laminate or the like, as well as combinations thereof. Examples of a nonwoven fabric useable in the body side liner or topsheet 44 include, for example, an airlaid nonwoven web, spunbond nonwoven web, meltblown nonwoven web, a bonded-carded-web, hydroentangled nonwoven webs, spunlace webs or the like, as well as combinations thereof. Other examples of suitable materials for constructing the body side liner or topsheet 44 can include rayon, bonded carded webs of polyester, polypropylene, polyethylene, nylon, or other heat-bondable fibers finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat bondable materials.

Other examples of suitable materials for the body side liner or topsheet 44 are composite materials of a polymer and a nonwoven fabric material. The composite materials are typically in the form of integral sheets generally formed by the extrusion of a polymer onto a nonwoven web, such as a spunbond material. In a desired arrangement, the body side liner or body contacting layer 44 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the body side liner or body contacting layer and penetrate into the other components of the article (e.g., into the absorbent core 48). The selected arrangement of liquid-permeability is desirably present at least on an operative portion of the body side liner or topsheet 44 that is appointed for placement on the body-side of the article. The body side liner or topsheet 44 can provide comfort and conformability, and can function to direct bodily exudates away from the body and toward the absorbent core 48. The body side liner or topsheet 44 can be configured to retain little or no liquid in its structure, and can be configured to provide a relatively comfortable and non-irritating surface next to the body-tissue of a wearer.

The baffle or backsheet 46 may include a layer constructed of any operative material, and may or may not have a selected level of liquid-permeability or liquid-impermeability, as desired. In a particular configuration, the baffle or backsheet 46 may be configured to provide an operatively liquid-impermeable baffle structure. The baffle or backsheet 46 may, for example, include a polymeric film, a woven fabric, a nonwoven fabric or the like, as well as combinations or composites thereof. For example, the baffle may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Suitably, the baffle or backsheet 46 can operatively permit a sufficient passage of air and moisture vapor out of the article, particularly out of an absorbent (e.g. storage or absorbent core 48) while blocking the passage of bodily liquids. An example of a suitable baffle material can include a breathable, microporous film, such as those described in, for example, U.S. Pat. No. 6,045,900 to McCormack et al.

Bicomponent films or other multi-component films can also be used, as well as woven and/or nonwoven fabrics which have been treated to render them operatively liquid-impermeable. Other suitable baffle materials may be used, including closed cell polyolefin foams. For example, a closed cell polyethylene foam may be employed.

The liquid permeable body side liner 44 and the liquid-impermeable baffle 46 may be peripherally sealed together to enclose the absorbent core 48 to form the absorbent article 10. Alternatively, the body side liner or topsheet 44 can be wrapped around both the absorbent 48 and the baffle or backsheet 46 to form a wrapped pad. The body side liner 44 and baffle 46, and other components of the absorbent article, can be joined for example with adhesive bonds, ultrasonic bonds, thermal bonds, pinning, stitching or any other attachment techniques known in the art, as well as combinations thereof.

The absorbent core 48 is designed to absorb body exudates, including menstrual fluid, blood, urine, and other body fluids. The absorbent core 48 may contain one or more layers of absorbent material. The layers can contain similar materials or different materials. Suitable materials for the absorbent core 48 include, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A preferred material is wood pulp fluff for its low cost, relative ease of formation and good absorbent properties.

The absorbent core 48 can also be formed from a composite comprised of a hydrophilic material which may be formed from various natural or synthetic fibers, wood pulp fibers, regenerated cellulose or cotton fibers, or a blend of pulp and other fibers. A desired material is an airlaid material.

In one embodiment, the absorbent core 48 also includes a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Additional layers or substrates, including for example, the liquid acquisition and distribution layer 4, also referred to as a surge or transfer layer, and an optional tissue layer 6 are also incorporated into the absorbent article, for example, between the body side liner or topsheet 44 and the absorbent core 48. The distribution layer 4 may be shorter than the absorbent core 48 or have the same length as the absorbent core 48. The distribution layer serves to temporarily hold an insulting fluid to allow the absorbent core sufficient time to absorb the fluid, especially when a superabsorbent material is present. In one embodiment, the absorbent core, distribution layer and other components, such as tissue layers, are free floating (unattached) between the outer cover and the liner, which are secured along only the peripheral edges thereof. Alternatively, the absorbent core, transfer layer and other components are attached to one or both of the outer cover and liner and/or to each other.

Referring to FIGS. 3, 5 and 6, the absorbent article 10 is shown in a folded configuration. For example, the absorbent article can be folded along a pair of fold lines 30, 32 to form a tri-fold configuration. In other embodiments, the absorbent article can be bi-folded, flat or rolled. The absorbent article is then inserted into an individual packaging component, otherwise referred to as an inner wrapper component, a wrapper or pouch. Alternatively, a plurality (meaning two or more) of article components may be disposed in a single pouch, and a plurality of pouches can be disposed in a package (shown in FIG. 4), otherwise referred to as an outer packaging component. One article/packaging configuration is shown in U.S. Pat. No. 6,601,706 to McManus, which is hereby incorporated by reference. The articles can be oriented in various ways within the individual packaging component, for example with the fold lines 30, 32 running parallel or perpendicular to the sides of the packaging component 68, 70.

In one embodiment, the wrapper component is formed as a portion of the article component. For example, an outer cover, such as the baffle material, can form a packaging component, as shown for example in U.S. Pat. No. 5,993,430, which is hereby incorporated herein by reference. It should be understood that in these embodiments, the article component is considered to be disposed in the packaging component when the packaging element is sealed or otherwise closed. In other embodiments, the article component is rolled, with a flap portion of a packaging component overlying a panel portion of the packaging component, regardless of whether the packaging component is integral with the article component or separate therefrom.

Although the wrapper component may have different configurations or can be prepared in other ways without departing from the scope of the present invention, referring to FIGS. 1, 2 and 3, the wrapper component may have pouch 50 formed from a strip or web 52 of material having a first and second ends having free edge 54, 56. It should be understood that the term "free edge" refers to an edge that is unattached after the package component is opened, regardless of whether the free edge is attached when the package component is closed. Accordingly, one or both of the free edges may be formed along a perforation line, or may be adhered to an underlying layer, with the edge defined by the perforation line being a "free edge" after the perforation line is broken. The free edge can be a single layer cut or formed edge, or can include a double-layer folded edge, or can include an edge formed by a plurality of layers. The pouch material can be formed from a non-woven material, films, paper, laminates, and/or cloth (including woven) materials, and combinations thereof. For example, the pouch can be made as disclosed in U.S. Pat. No. 6,716,203, to Sorebo et al., the entire disclosure of which is hereby incorporated herein by reference. In one embodiment, the pouch is made of a film/spunbond laminate material available from Kimberly-Clark Corp, and know as HBSTL ("highly breathable stretch thermal laminate"), and which material is further disclosed in U.S. Pat. No. 6,276,032, to Nortman et al., the entire disclosure of which is hereby incorporated herein by reference. Various embodiments of a nonwoven pouch material can have a basis weight less than about 50 gsm, alternatively between about 10 gsm and about 40 gsm.

Each of the first and second ends is folded along fold lines 58, 60 that define the top and bottom edge of the pouch respectively. The folded pouch has a back panel 62, a first panel 64 and a second panel 66. The first panel 64 and back panel 62 are secured along side edges 68, 70 thereof to form a pocket shaped to receive the absorbent article. In one embodiment, the pocket and pouch are shaped and dimensioned to receive a single article component, which is individually wrapped in the pouch. The second panel 66 is folded over the first panel 64 such that the free edge 54 of the second panel overlies the first panel 64. In this configuration, the second panel 66 acts as a flap. The first panel 64 has a covered or overlap portion 57 extending between the free edge 54 (exterior) and the free edge 56 (interior), which covered or overlapped portion 57 underlies the second panel. In one embodiment, there is no overlap, rather, the free edges 54, 56 abut or are separated by a small distance. In one example, the portion 57 has a length of about 0 about 50 mm, generally about 2-22 mm and typically about 4-10 mm between the free edges 54, 56. In various embodiments, the overlap distance is less than or equal to about 95% of the overall packaging component length in a closed configuration, more desirable less than or equal to about 35% of the packaging component length, and more desirably less than or equal to about 20% of the packaging component length. In various embodiments, the free edge 54 is positioned a distance from either edge 58, 60 that is greater than or equal to about 10% of the overall length of the packaging component (in a closed configuration), more desirably greater than or equal to about 30%, and more desirably about 50% of the packaging component length. The first panel further includes an uncovered second portion 59 extending between the free edge 54 and the bottom edge 58. Of course, it should be understood that the length and width of the article and packaging components can vary according to the type of article and the size of the article.

As an alternative to having the free edge 54 of the second panel 66 overlap the first panel, the wrapper component can be designed such that there is no overlap between the free edge 54 and the first panel 64, without departing from the scope of the present invention. For example, the free edges 54, 56 may abut each other or are separated by a small distance such that there is a gap between the free edges (not shown). As such, in this alternative, the second panel is defined merely as another panel.

A pair of side seals 74 secures the first panel 64 to the back 62, and the second panel 66 to the back 62 and to the first panel 64. The side seals are desirably formed after the first panel is folded over the back panel and the second panel is folded over the back panel and the first panel. Although, it is possible that the first panel could first be sealed to the back panel, and the second panel then sealed to one or both of the back panel and first panel. In an alternative configuration, the second panel is not sealed at the side edges of the first panel and back panel. This embodiment is described in more detail below. The sides may be sealed by any method known to those skilled in the art. Exemplary sealing methods include, for example, adhesive sealing, bonding by the application of heat and pressure, ultrasonic bonding or any other art known bonding methods. In one embodiment of the present invention, the side seals 74 may be frangible, meaning they can be easily broken such that the second panel 66 can be separated from the first panel 64 and back panel 62, and such that the first panel 64 can be easily separated from the back panel 62, wherein the product component 10 is exposed for removal from the pouch by the user.

In one embodiment, the second panel 66 is releasably secured to the first panel 64. For example, a fastening element 72, shown as a tab in FIGS. 1 and 2, is secured across the free edge 54 of the second panel 66 to secure the second panel 66 to the first panel 64. The fastening element can be releasably secured to both of the second panel and first panel, or it can be fixedly secured to one of the second panel and first panel and releasably secured to the other. Other possible configuration include that the fastening element is fixedly secured to both panels and one or both of the panels is provided with an area of weakness, such as a perforated area, which allows a portion of one or both of the panels to be removed or damaged when the wrapper is opened. The fastening element can be formed as adhesive tape, a snap, a button, a mechanical fastener (e.g., hook and loop), a tie, or as any other device known by those skilled in the art. The fastening element can have various alternative shapes, including but not limited to a square, rectangle, triangle, circle, oval, obround, oblong or diamond shape, or any other irregular shape or pattern. In an alternative embodiment, the fastening element is formed on the inside of the second panel such that it engages the first panel as the second panel is folded thereover and is not visible to the user. For example, the fastening of the second panel 66 to the first panel 64 may be accomplished by the use of an adhesive applied to the side of the second panel 66 which contacts the first panel 64, to the side of the first panel 64 which contacts the second panel 66, or both. This adhesive may be applied as a ribbon, dot, a swirl pattern or any other pattern which effectively adheres the second panel 66 to the first panel 64. In another alternative way to fasten the second panel 66 to the first panel 64, the second panel 66 is simply sealed to the first panel 64 with a heat seal or other weld, with the weld defining the fastening element. In another embodiment, the second panel 66 is not sealed or otherwise attached to the first panel 64, but rather is simply folded thereover. Alternatively, the sides of the second panel are sealed to the back panel and to the first panel, with the side seals being breakable in response to a user grasping and lifting the second panel. It is within the scope of the present invention that the sensory cue could be located on the fastening element.

In some embodiments, the second panel 66 is refastenably secured to the first panel 64, while in others, the second panel is not intended to be secured to the first panel once the packaging component is opened. For example, in one embodiment, the free edge 54 of the second panel 66 is defined by a perforation line, with the second panel not being refastenable after the perforation is broken.

Referring to FIG. 4, a plurality of absorbent articles 10, whether individually wrapped as shown in FIGS. 1-3, or left unwrapped, are packaged in an outer packaging or bulk packaging component 76, meaning a component capable of holding two or more absorbent articles. The outer or bulk packaging component 76 is typically the packaging used to provide the absorbent products to consumers on store shelves. The outer or bulk packaging typically provided consumers with a convenient means to transport the absorbent articles from the retailer to their home or other place of use. In one embodiment, the packaging component is formed as a bag having at least one side seal 78 securing a pair of edges of the bag together. In other embodiments, the plurality of absorbent articles is packaged in a box or carton. The bags may be prepared from a non-woven material, polymer film, paper, laminate, and/or cloth (including woven) materials, and combinations thereof. Boxes or cartons may be prepared from materials such as cardboard, paperboard and the like.

In the present invention, the personal care product may have a packaging component and absorbent article component that are coordinated with each other. Coordination may be achieved using certain combinations of visual characteristics which unite or harmonize the appearance of an absorbent personal care article with a packaging component. Coordination may be achieved by matching visual characteristics of the packaging and article components or by causing the components to be matched. As described above, visual characteristics are features or characteristics that are discernible by sight during the normal use of the product. Examples of different types of visual characteristics, which may be employed in the present invention include, without limitation, color, form, texture, pattern, transmittance/opacity, gloss, and sheen, among others.

Of the visual characteristics, color is a characteristic that is simple to quantify. Colors have some basic characteristics, including hue, saturation, and luminosity. Each of these terms is described above. A given color may be varied by changing the saturation and luminosity. Saturation is changed by adding a neutral color, black, white, or gray. Luminosity may be changed by adding a brightener to a given color. Again, each of these terms is defined above. In the present invention, if two colors have the same hue, whether or not they are different in saturation or luminosity, the two colors are considered coordinated. Likewise, if two colors have the same saturation or the same luminosity, the colors are considered to be coordinated. Colors which have the same hue, saturation and luminosity are considered matched. Color may be imparted by any means know to those skilled in the art, including, for example, printing, dyeing, pigmenting and the like.

Form may be accomplished by techniques know to those skilled in the art. Form can be construed on the simplest scale as shape. Shape may be imparted to the components by know methods such as cutting and the like. By using the term "shape" in this context, it is intended that the outline, edges and the like have a shape in addition to a linear outline. Generally, shapes are considered the same if the aspects of one shape are proportional to another shape. For example, in the case of a triangle, if all the angles are identical in two different triangles, but the sides are different in length, the two triangles are considered to be coordinated since they have the same proportions relative to each other. Stated another way, shapes are considered to be coordinated if the shapes are the same or are proportional to each other. In the present invention, the shape or form of the wrapper or some aspect of the wrapper, for example the second panel or opening, could have a shape associated with one or more elements of the article component, for example the shape of the ends of the peel strip.

Textures can be visual effects generated by rough surfaces, and or differences in the surface characteristics, or visual illusions created by mere color or pattern. Texture may be the result of the natural characteristics of a given material as a result of the material formation process. Textures may also be imparted to a material using known techniques known to those skilled in the art including, for example, printing, embossing, bonding, aperturing and the like.

One or more objects, one or more geometric and non-geometric shapes and/or one or more colors having some relationship with one another may achieve patterns. Patterns may be random or repeating. Repeating patterns typically have objects, shapes, colors in a given frequency or spacing. Patterns can be achieved by repeating a single object, or shape or can be achieved by repeating multiple objects or shapes. Repeating or alternating two or more colors with a given frequency may also create patterns. Patterns may be formed by using techniques including, for example, printing, embossing, bonding, aperturing and the like.

Any known printing method may be used so long as a pattern or a texture can be imparted to the surface being printed. Embossing may be accomplished, for example, by passing a material between a heated or non-heated anvil roll and a heated or non-heated embossing roll, with the embossing roll containing a pattern. Other techniques for imparting patterns or texture include, for example, aperturing, creating layers, orientation of materials, bonding patterns and the like. Texture can also be created by selection of materials having the same or similar visual characteristic, beyond color, and patterns imposed on the material.

Other visual characteristics that may be used in the present invention include, for example, transmittance/opacity, gloss, and sheen of the materials used to produce the components.

In the simplest form of the present invention, the visually coordinated absorbent product has at least a first element and a second element, each element comprises at least a first and second visual characteristic, wherein the first and second visual characteristics are different from each other and the first and second visual characteristic of the first element are matched to the first and second visual characteristics of the second element. As an example, a wrapper component has a pattern of purple printed flowers thereon and an element of the absorbent article, for example the peel strip or the baffle may have the same pattern of purple flowers printed thereon. The pattern of flowers is a first visual characteristic and the purple hue of the flowers is a second visual characteristic. As a result, the absorbent article is coordinated with the packaging component due to the presence of the pattern of purple flowers on both components. Coordination of the product in the present invention is obtained by having two or more components with two or more visual characteristics that match, or caused to match one another. While the present specification describes the invention in terms of first and second visual characteristics, this does not mean that there cannot be more than two visual characteristics creating the desired coordination affect. In fact, the more shared visual characteristic there are, the more items appear to be coordinated. In the present invention, there may be two, three, four, five, six, seven, eight, nine or more visual characteristic which are coordinated. In one aspect of the present invention, there are at least six visual characteristics that are coordinated, and desirably at least nine characteristics that are coordinated.

As is set forth above, the first and second visual characteristics must be different in some aspect. It is possible for the visual characteristics to be two different colors, a color and a pattern, a texture and a color, a texture and a pattern, two different patterns, two different textures and the like. If there are three characteristics which are different, then there could be two different colors and a pattern; three different colors; a color, a pattern and a texture; among many other combinations.

In one aspect of the present invention, white is generally not considered as a color is used as the coordinating feature if white is a predominate color on the element being coordinated. This is because white is the predominate color of personal care articles white do not lend itself as a coordinating color. However, white may be a coordinating color, provided that it is not used as the predominate color on the components or surfaces being coordinated. Stated another way, white may be a coordinating color if it is used as an accent or a non-dominate color. By "non-dominate color" it is intended mean a color which encompasses less than 50%, desirable less that 30%, of the surface area of a surface. Most desirably, white is not used as a coordinating color.

As explained above, in one embodiment, the first and second visual characteristics may be configured as first and second colors. Desirably, each of the first and second colors is different from one another by having a different hue. One or more colors may also be different by virtue of having a different luminosity and/or saturation/vividness. Saturation/vividness is the intensity of the color from pale to dark. Colors of different hues can be coordinated or match by virtue of having the same luminosity or saturation. For example, pale or pastel colors of different hues tend to blend together or appear that they belong together or are matched due to the fact that the saturation levels are similar. Other factors in color differences include different finishes e.g. gloss/finish verses a matte finish. Matte finishes tend to diffuse or scatter light compared to a gloss finish, which is specular.

At the same time, the first color of the personal care article component, such as the absorbent article, can be coordinated with the first color of one or both of the packaging components. In one embodiment, the second color of the personal care article component, such as the absorbent article, is also coordinated with the second color of one or both of the packaging components. The coordination of the colors is most desirable at distances of less than two feet, such that it is visible to the user of the article. At the same time, the coordination can provide a disguising aspect that is effective for an observer who is greater than 2 to 3 feet away from the article.

Figure 13:
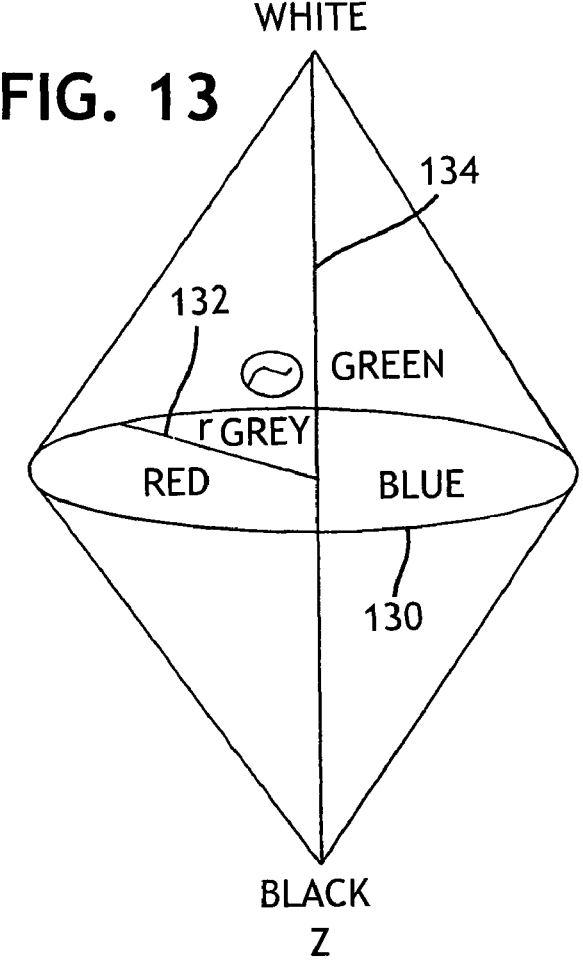
FIG. 13 is a schematic graphical illustration of color hue, luminosity and saturation/vividness.

Referring to FIG. 13, hue is measured by the angular position around the circle 110. Two colors are considered coordinated if they have first and second hues that are within about ±120 degrees of each other on the circle 13, alternatively within ±30 degrees, alternatively within ±15 degrees, alternatively within ±10 degrees, alternatively within ±5 degrees of each other, or alternatively within ±0.50 degrees of each other. Colors of different hues are also considered coordinated if they have a value (luminosity) difference of less than about 5% of maximum, alternatively less than about 3.0% of maximum or alternatively less than about 1% of maximum. Colors of different hues are also considered coordinated if they have a saturation difference of less than about 5% of maximum, alternatively less than about 3.0% of maximum or alternatively less than about 2.5% of maximum.

The hue, luminosity and saturation/vividness are measured as follows using the following equipment calibrated in the following way.

Equipment

Quantitative calorimetric measurements are typically made using a colorimeter or spectrophotometer. However, these instruments typically have large apertures (~1 cm) requiring a large color block for meaningful determination, making them unsuitable for color determination of graphics that may be composed of narrow lines or points whose width is much less than the instrument aperture. Therefore, a Zeiss KS400 Image Analysis system was used for feature identification and colorimetric measurement.

The Zeiss KS400 used a Zeiss AxioCam color CCD camera (1300×1030 pixels, 3 channel color, 8 bit per channel) equipped with a 20 mm AF-Nikkor lens (f/2.8). The camera was mounted vertically facing down onto a sample stage and had an effective field of view was 97×80 mm. Incident sample stage illumination was by four incandescent floodlamps (Sylvania) on a double Variac (70%; 90%), resulting in an illuminance of approximately 11,000 lux. The lamps were above the left and right edges of the sample stage directed towards the field of view at approximately 45 degrees.

Calibration

The camera black reference was with the lens cap on. The camera white reference was a Polaroid 803 positive with 15 ms exposure. To account for the warm color illumination bias of the floodlamps, the red, green, and blue (RGB) values were offset using the white selection tool in the KS400 software, resulting in corrected RGB values that yielded a white image.

Sample Setup and Image Acquisition

Samples are placed on the stage (normal viewing angle) and under ¼" plate glass to minimize topographical effects. Images of the color-bearing graphical portion are acquired at 15 ms exposure.

Image Analysis

Image analysis is performed in Matlab (v.6.5.1, release 13; Mathworks, Inc) with the Image Processing Toolbox (v4.0). RGB images were converted to hue, saturation, and value (HSV) space using Matlab's hsv2rgb.m command. Choosing a saturation lower limit of 0.05 (0-1 scale) resulted in practical detection of all the colored/inked portions of the graphic. The hue, saturation, and value (i.e. luminosity) densiometric distributions were calculated for the detected regions in each image.

As an example, colors of different hues but with similar saturation levels appear to be coordinated. As an example, pastel colors appear to be coordinated, even though the hues are different. Likewise, color of different hues but with similar luminosity or vividness levels appear to be coordinated, with one another Coordination in the present invention may also contain commonly used color schemes which tend to harmonize or coordinate. That is, the first and second visual color characteristics may be selected to enhance the visual coordination in addition to having at least a first and second color as the first and second visual characteristics. Examples of these color schemes include, for example, monochromatic color, complementary colors, analogous colors, warm and cool colors, neutral colors, color contrast, tetradic color scheme, triad color scheme or other chord color schemes. Monochromatic color scheme uses one base color but varies the color tint, shade and/or tone. Complementary colors are colors which are opposite each other on a color wheel. Analogous colors are colors which are adjacent each other on the color wheel. Warm and cool color schemes use three colors, two of which are warm colors and one is cool color or two cool colors and one warm color. Warm colors are generally associated with fire and the sun, for example, red, yellow and orange and cool colors are generally associated with water the sky and foliage, for example green, blue and violet. Neutral color coordination includes using shades of black, white, gray and beige together. Color contrast scheme include using dark and light colors together. Tetradic is a four color scheme and a triad color scheme is a three color scheme, both of which are known to those skilled in the art. Any of these color schemes may be used in the present invention to help coordinate and harmonize two or more colors as the visual characteristics in the present invention.

Coordination may be created by providing a theme on the absorbent article and packaging component. Possible themes include, for example, femininity, security, protection, or emotional themes such as friendship, purity, natural among others.

Figure 10:
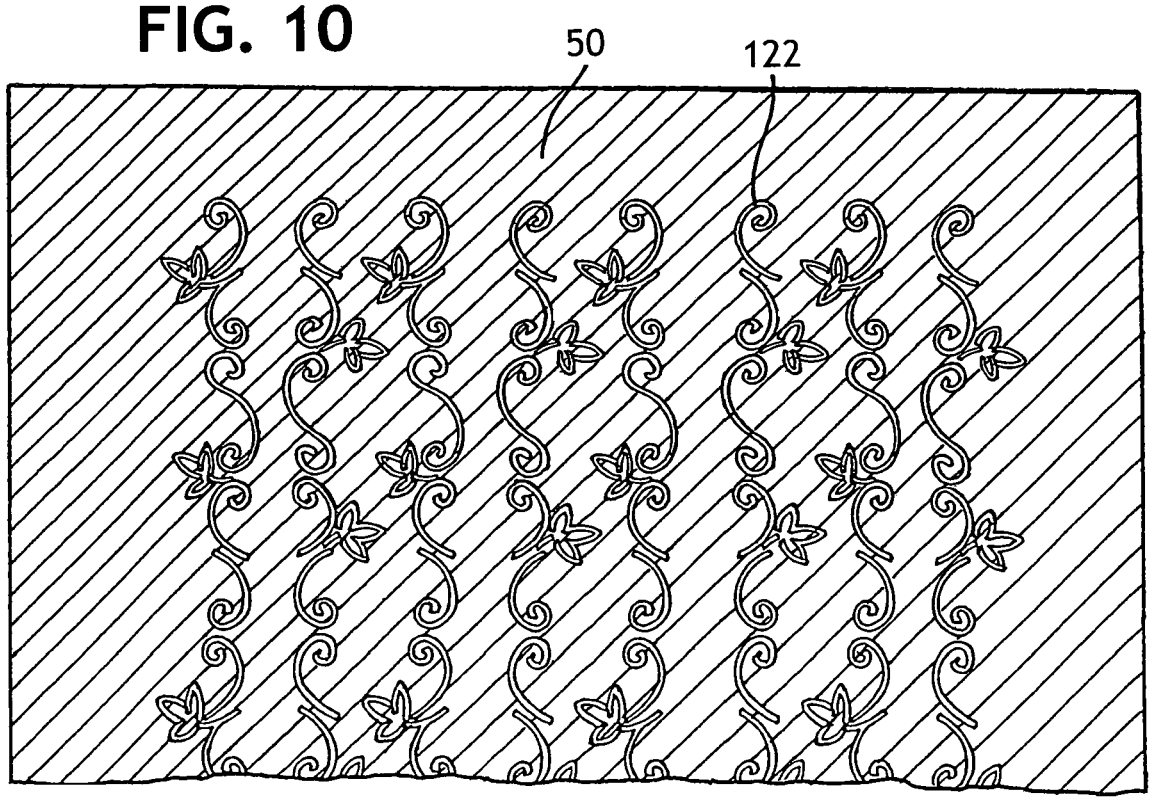
FIG. 10 is a portion of one embodiment of a packaging component having a pattern thereon.

Two patterns are considered coordinated when they have substantially the same pattern elements, regardless of other factors such as orientation. To gain a better understanding of how patterns are considered to be coordinated within the scope of the present invention, reference is made to FIGS. 9-12. In FIG. 9, an element of an absorbent personal care product, in this case a peel strip 28, is configured with a pattern 122, in the case shown, the pattern is a pattern of ivy. FIG. 10 shows another element of an absorbent person care product, in this case the packaging component 50, which is configured with a coordinated pattern 122 of ivy. The patterns 122 are coordinated, i.e., substantially the same shape, even thought they are of different sizes. Summarily, referring to FIGS. 11 and 12, an element of the personal care product, a peel strip 28, is configured with a pattern 126, 146 of tulips and scrolls, while the packaging component 50 is configured with a coordinated pattern 126, 146 of tulips and scrolls. The patterns 126, 146 are coordinated, i.e., substantially the same shape, even though they are of different sizes and notwithstanding that additional pattern elements 128, 130 are also present on the packaging component 50. Stated another way, in the present invention, two patterns are considered coordinated if the patterns have the same or similar pattern elements, whether the patterns are matched identically or similarly matched, by having the same pattern but being of a different size. It is further noted that patterns are considered coordinated if there are pattern elements which are the same or similar, even if additional pattern elements are present.

In one embodiment of the present invention, there are at least two different types of visual characteristics. One particular combination is the use of color and pattern. As set forth above, the more shared visual characteristics there are, the more coordinated the personal care article and packaging component will appear.

In the present invention, when color or patterns are used and are printed, the color or pattern may be printed on the outer surface, on an inner surface or between surfaces. For example, in the case of the garment side outer cover, the color or pattern may be applied to the side of the garment side outer cover which is positioned during use adjacent the garment or may be applied to the side of the garment side outer cover which is proximate the absorbent core. Alternatively, if the garment side outer cover is a multilayer structure, the color or pattern may be printed between the layers. Another alternative for obtaining color or a pattern on the personal care article is to apply any adhesive used to hold layers of the absorbent article together with a colored adhesive or to apply the adhesive in a pattern. The same is true with the wrapper. The color or pattern may be applied to the outside surface of the wrapper, on the inside surface of the wrapper or between layers of the wrapper if the wrapper has multiply layers.

In order to obtain a better understanding of the present invention, attention is directed to FIGS. 1-3. In these figures, the packaging component 50 has at least a first and second visual characteristic. For example, the wrapper 52, preferably an outer surface 78 thereof including for example the back 62, second panel 66 and the portion of the first panel 64 not covered by the second panel, may have a first color and the outer surface of the fastening element 72 may have a second color, or the outer surface of the wrapper 52 may have a plurality of colors, including a first and second color. Alternatively, a portion or the entirety of the outer surface of the wrapper 52 may have an embossed pattern or printing applied thereto, which may include one or more shapes. Accordingly, in various exemplary embodiments, the first visual characteristic may be a color and the second visual characteristic may be a different color, with one or both of the colors applied to the wrapper and/or fastening element. In another embodiment, the first visual characteristic may be a color, and the second visual characteristic may be an embossment, pattern, shape (e.g., fastening element) or side seal. In yet another embodiment, the first visual characteristic may be a first embossment, printing or dyeing pattern and the second visual characteristic may be a second embossment, printing or dyeing pattern.

Referring to FIG. 4, the bulk packaging component 76 also has at least a first and second visual characteristic. For example, the outer surface 80 of packaging component may have one or more colors, printings, side seal configurations, etc. In a desired embodiment, the first and second visual characteristics of the bulk packaging component are correspond to and are coordinated with the first and second visual characteristics of the individual packaging component.

Referring to FIGS. 3, 5 and 6, the article component 10 also has at least a first and second visual characteristic that correspond to and are coordinated with the first and second visual characteristics of one or both of packaging components 50, 76. For example, a portion of one or more of the outer cover 46, peel strip 28, absorbent core 48, distribution layer 4 or tissue layer 6 has a first visual characteristic, while another portion thereof, or another element, has a second visual characteristic, with the first and second visual characteristics corresponding to and being coordinated with the first and second visual characteristics of one or both of the packaging components. In various embodiments, portions of the absorbent core, surge layer and/or tissue layer, or any other substrate disposed between the liner and outer cover, are visible through the liner, which is at least partially see-through, while in other layers such interior components may not be visible. In addition, a body-side surface of the outer cover may be visible through the liner and/or absorbent core on the body-side surface of the absorbent article.

In one embodiment, the outer cover 46 and the wrapper 52 are the same first color, while the outer surface of the peel strip 28 and the fastening element 72 are the same second color, meaning the colors have similar hues or matched hues., saturation and/or luminosity, or combinations thereof, as defined below. At the same time, the first and second colors of the article component are different from each other, meaning that the colors have different hues, saturation and/or luminosity, or combinations thereof. In another embodiment, the outer cover 46 and the fastening element 72 are the same first color, while the outer surface of the peel strip 28 and the wrapper 52 are the same color. The various colors include without limitation white, black, yellow, orange, purple, green, red, blue, and pink. In other embodiments, one of the core 48, surge layer 4 and tissue layer 6 are a first color, desirably non-white, which is visible to the user through the liner 44 and which corresponds to a first color of the wrapper 52, article component 76 and/or fastener element 72. For example, the outer cover can be configured as a purple, blue, pink or green, with the absorbent core being white or some other different color, and with one or both of the surge layer and tissue layer also being purple, blue, pink or green. At the same time, one of the wrapper and fastening element are made purple, blue, pink or green, with the other of the wrapper and fastening element being white or the other different color. In other embodiments, one of the article and/or packaging components can have a color gradient, wherein the color transitions from one color to another, or one or more of the properties thereof changes over a distance.

In other embodiments, the liner, peel strip or outer cover are provided with an embossment (i.e., macro-embossing that is discernable to the user) or a printing or dyeing pattern that corresponds to an embossment or printing pattern on the wrapper, fastening element or packaging component.

Of course, it should be understood that the packaging components 52, 76 and article components 10 could have more than two coordinated visual characteristics, including for example three characteristics such as a pair of colors and an embossment and/or printing/dyeing, or three colors, or any combination of the visual characteristics set forth above or otherwise known in the art.

In one embodiment, and referring to FIGS. 3 and 5, the packaging component 50 is made of a combination of blue fibers. The blue of the fibers has a consistent hue but the process of adding the blue to the fibers creates blue fibers of varying saturation. So, the fibers appear to vary in vividness with some of the fibers almost appearing white and the pouch appearing as a random assortment of blues. This random assortment of blues allow the packaging component 50 to coordinate to the various colors in the article component 10 elements, for example a white peel strip 28 and blue baffle 46. For example, in one embodiment, the difference in the hue between the outer surface of the baffle, which is blue, and the pouch, which is blue, is 13.6 degrees and the difference in the value (luminosity) is 0.6% of maximum.

This coordination also allows the packaging component to hide or obscure the article component disposed therein. In essence, the coordination leads the observer (standing 2 or more feet away—as opposed to the user standing within 2 feet of the article) to consider the packaging and article components as a single unit, rather than as two separate units. Therefore, the observer has a more difficult time distinguishing the pad within the pouch. In this way, the coordination serves a dual purpose of providing a more aesthetically appealing article to the user, while hiding the article from observers or non-users.

Referring to FIGS. 7-12, different embodiments of various article and packaging components are shown with various coordinating visual characteristics. For example, as shown in FIG. 7, the absorbent article 50 is shown as having a pattern of alternating strips 110, 112 of first and second colors. Likewise, the packaging component 50 has the same pattern of alternating strips 110, 112 in the same colors. It should be understood that two patterns are coordinated if they both have at least one substantially identical element, or if the overall distribution of elements in a certain region is substantially identical. Therefore, and for example, the patterns of the article and packaging components in FIG. 7 are coordinated in two ways, (1) each component has a substantially identical element (e.g., one of the stripes 110, 112) and (2) both components have a substantially identical distribution of elements 110, 112 thereover, i.e., a plurality of similarly dimensioned stripes alternating in color. For example, a checker board pattern would be coordinated by the shape of the individual elements (squares) as well as by the overall distribution thereof (alternating colors and positioning). It should be understood that for the first type of pattern coordination (substantially identical elements), the elements do not have to be of the same size or oriented in the same orientation, but rather that they merely have substantially the same shape. With the respect to the second type of pattern coordination, the individual elements do not even have to have the same shape, as long as the overall distribution is coordinated. It should be understood that the article and packaging components 10, and 50, respectively of FIG. 7 are also coordinated by way of the colors of the stripes, which have one or more coordinated hues, luminosities and saturation/vividness values.

Referring to FIG. 8, the article component 110 is coordinated with the first packaging component 50 first by way of the colors of the pattern element 120 and the pattern element 110 and second by way of the color of the backsheet 46 and the pattern element 112. The article component 50 is coordinated with the second packaging component 118 first by way of the pattern elements 120, second by way of the color of the pattern elements 120, and third by way of the color of the backsheet 46 and color of the base sheet 140.

Referring to FIGS. 9 and 10, a peel strip 28 is configured with a pattern 122 of ivy, while the packaging component 50 is configured with a coordinated pattern 122 of ivy. As described above, the patterns 122 are coordinated. The peel strip 28 is further coordinated with the packaging component 10 by way of the color of the pattern 122 on the peel strip with the color of the background on the packaging component, which are both blue for example with coordinated colors, including for example hues, saturations and/or luminosities, or combinations thereof. Likewise, the color of the background of the peel strip 28 is coordinated with the color of the ivy pattern 122 on the packaging component.

Figure 11:
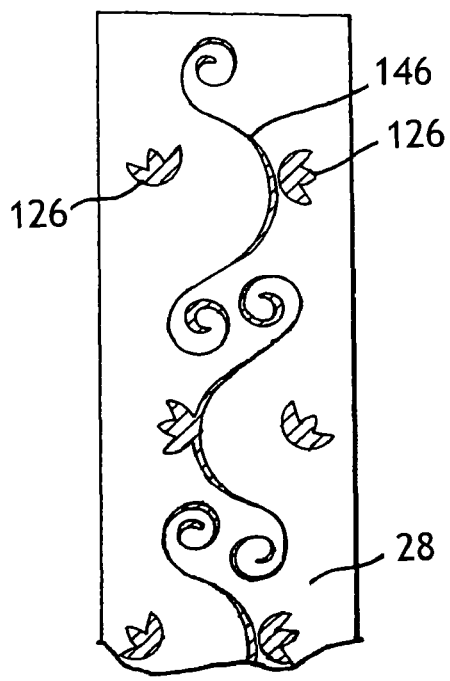
FIG. 11 is another embodiment of a peel strip having a pattern thereon.
Figure 12:
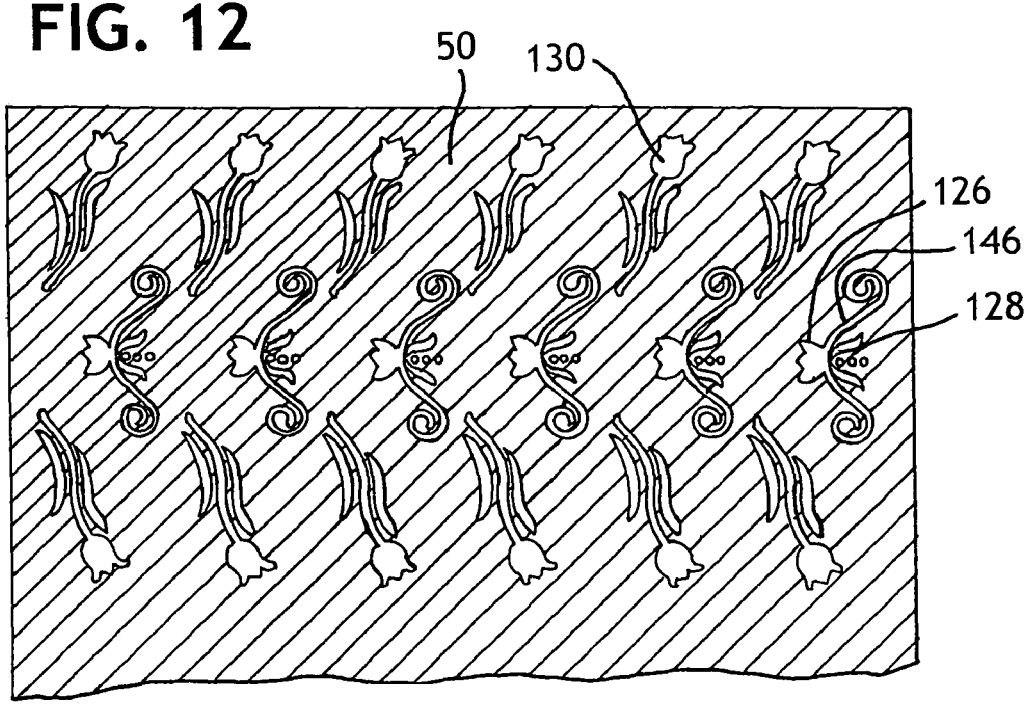
FIG. 12 is a portion of another embodiment of a wrapper component having a pattern thereon.

Referring to FIGS. 11 and 12, a peel strip 28 is configured with a pattern 126, 146 of tulips and scrolls, while the packaging component 50 is configured with a coordinated pattern 126, 146 of tulips and scrolls as described above. The peel strip 28 is further coordinated with the packaging component 10 by way of the color of the patterns 126, 146 on the peel strip with the color of the background on the packaging component, which are both blue for example with coordinated colors, including for example hues, saturations and/or luminosities, or combinations thereof. Likewise, the color of the background of the peel strip 28 is coordinated with the color of the patterns 126, 146, 128 and 130 on the packaging component.

Figure 15A:
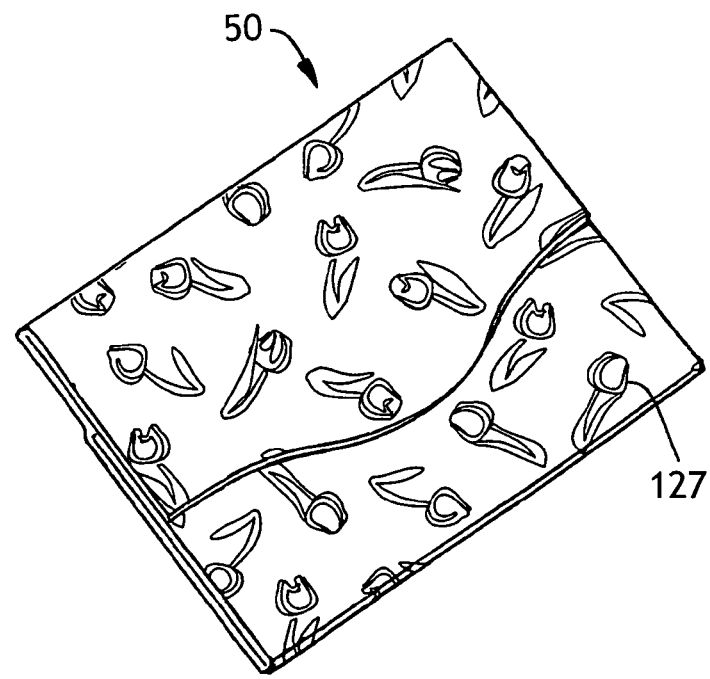
FIGS. 15A and 15B shows an example of an embodiment of the present invention wherein the peel strip and wrapper component are matched.
Figure 15B:
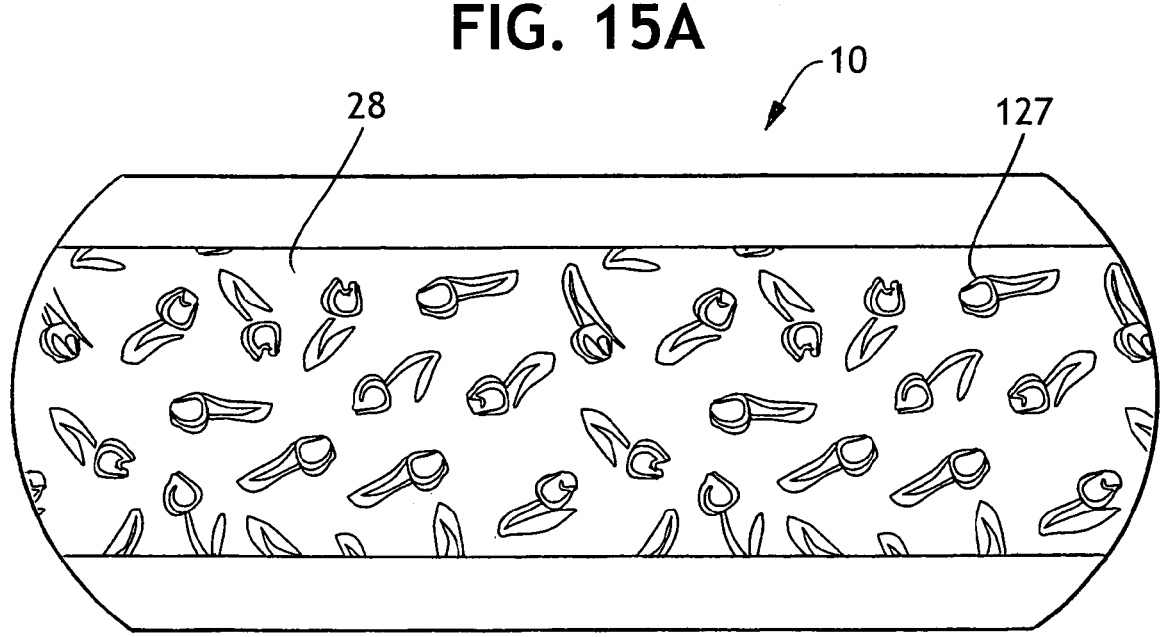

FIGS. 15A and 15B show an exemplary product of the present invention with coordinating pattern and color. FIG. 15A shows a wrapper packaging component 50 having a pattern of flowers 127 which have a color hue. FIG. 15B show an absorbent product 10 has a peel strip 28 which has the same pattern of flowers 127 of the same hue. As can be scene, the peel strip 28 and the packaging component have a matched pattern.

Figure 16A:
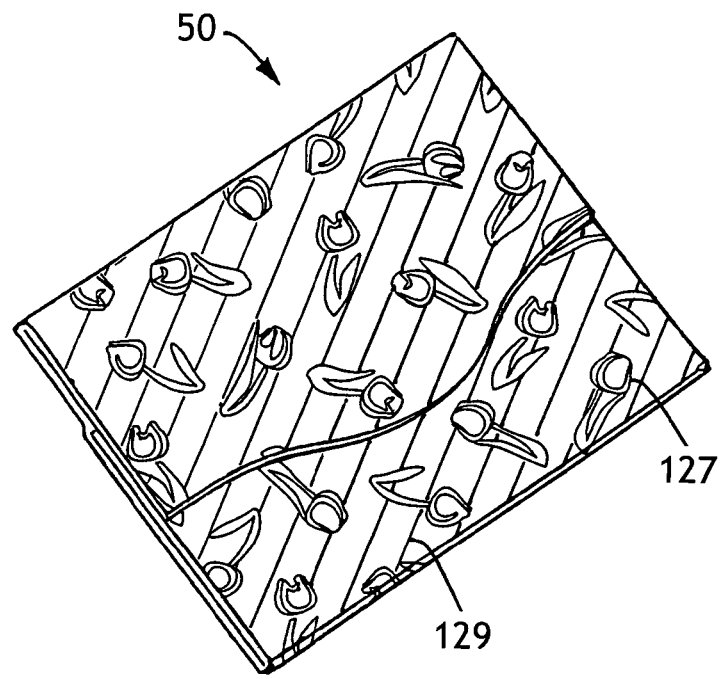
FIGS. 16A and 16B shows an example of an embodiment of the present invention wherein the absorbent article, peel strip and wrapper component are caused to match.
Figure 16B:
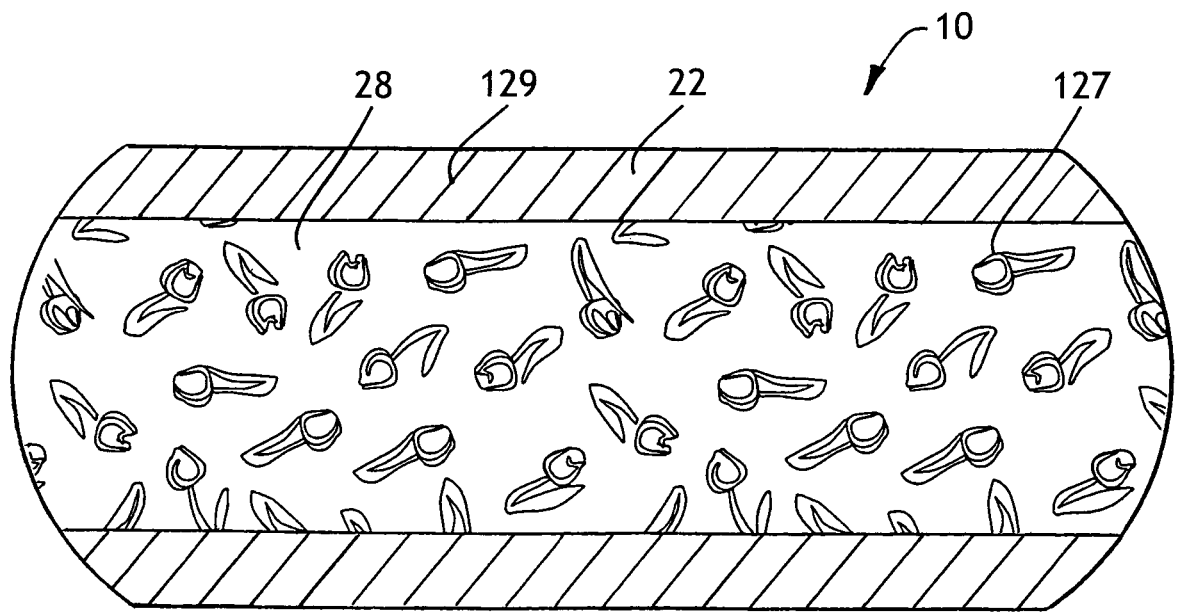

FIGS. 16A and 16B show an exemplary product of the present invention having a absorbent article 10 with a peel strip 28 and a packaging component being caused to coordinate. FIG. 16A shows a wrapper packaging component 50 having a pattern of flowers 127 which have a color hue and a pattern or color 129 being used as the background for the pattern of flowers 127. FIG. 16B show an absorbent product 10 has a peel strip 28 which has the same pattern of flowers 127 and same hue as the pattern of flowers on the wrapper component 50. However, the peel strip does not have the pattern or color 129 applied thereto. The baffle 22 does have the pattern or color 129 applied thereto. As a result, the wrapper component 50, with its pattern of flowers 127 and pattern or color 129, causes the peel strip 28 to coordinate with the pattern or color 129 present on the baffle 22.

The coordination described above in reference to the FIGS. 1-12, 15 and 16 is merely used to show what is intended by coordination. The present invention goes beyond what is specifically shown in the FIGS. 1-12, 15 and 16. Other elements of the personal care article may also be coordinated and types of coordinating features will be described and coordination may be achieved using many different color schemes. Ideally, its is beneficial to coordinate the packaging and personal care article with objects, or items often associated with positive life experiences within a users life, such as floral displays in the case of feminine care articles. As is discussed above, the visual characteristics may be imparted in numerous ways including printing, embossing, bonding, aperturing, among others.

Embossing is an effective way to impart texture and pattern visual characteristics to a packaging component and absorbent article. Embossing can be used to promote a feminine flair to the absorbent articles without adding per unit cost to the articles produce, unlike printing. In the present invention, embossing of the pouch material enables a user to easily locate the pouch and absorbent article combination when the pouch in located in a purse, backpack or other similar personal object transporting means, when the absorbent article is out-or-sight. The embossing may be placed on the body facing side or garment side of the personal care article. In addition, the same or similar coordinating embossing pattern may be placed on the packaging component, including the outer packaging component and the pouch. The embossing pattern may be a high density embossing pattern, or a low density embossing pattern, both of which may be registered or non-registered. For further feminine flair, it is desirable that the embossing pattern be a soft pattern like floral elements.

Figure 14:
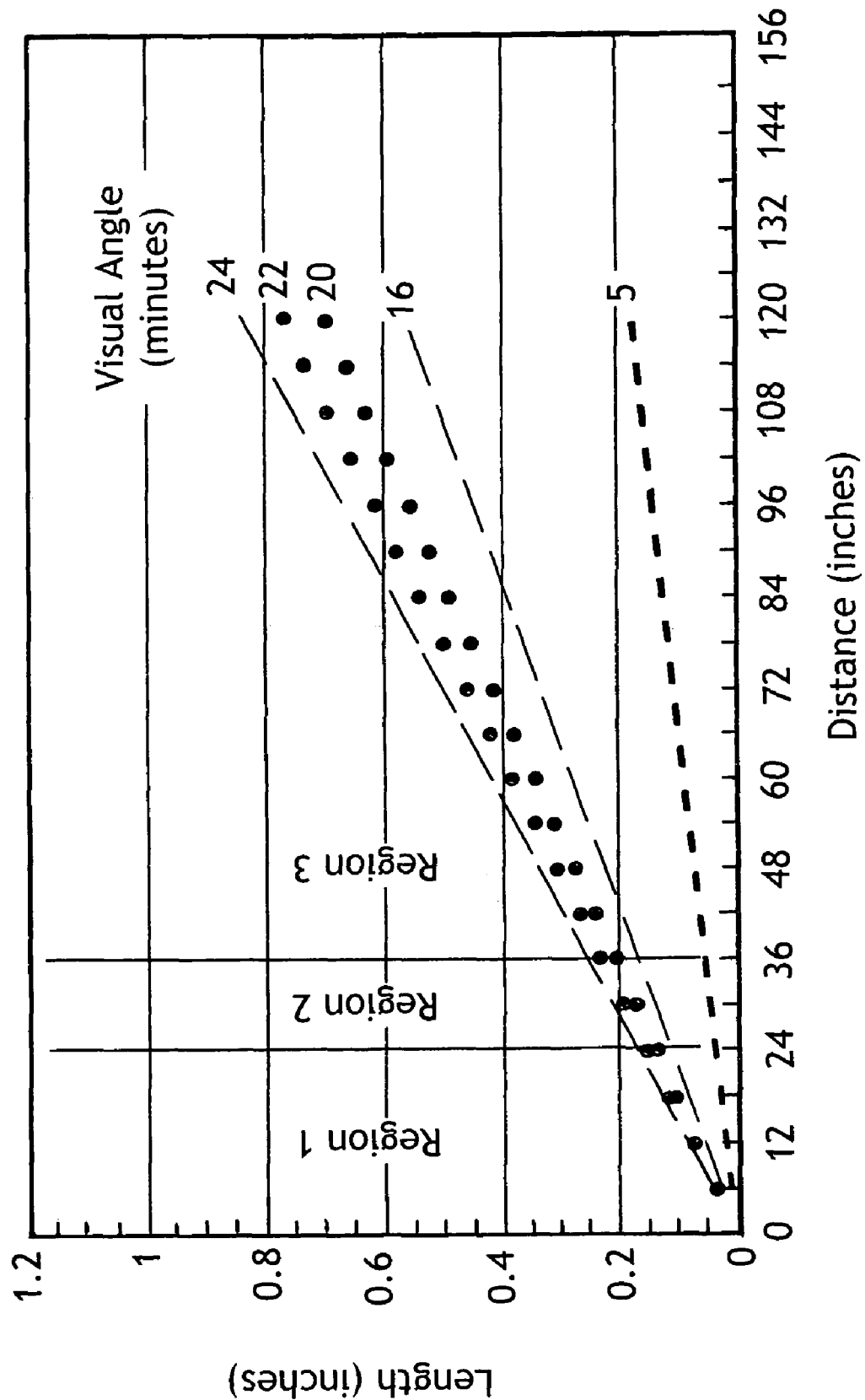
FIG. 14 shows the translation of a size of a pattern to visual angle based on distance.

In selecting of the size of patterns applied to the wrapper/packaging component, the following should be taken into consideration. The size can be adjusted according to the visual angle and the distance in which the object is viewed. Typically, the threshold of pattern recognition is about 5 minutes of an arc. Generally, it is desirable to have a visual angle in the range of about 16 to 24 minutes of arc and usually 20-22 minutes of arc. The size translated in linear dimensions for a pattern from the arc dimensions is shown in FIG. 14. As can be seen in this as the distance from a pattern increases, the size of the pattern or object must increase. Typically, there three regions for viewing personal care articles. Region 1 is less than two feet, in which the personal care article is typically only seen by the user of the personal care article. Region 2 is between two and three feet and is a region in which both the user and non-user of the personal care article may view the personal care article. Region 3 is beyond three feet, in which the personal care article is typically only viewed by a non-user. Therefore, selecting the size of the pattern on the personal care article or packaging should be made taking into account FIG. 14, depending if it is desirable for a non-user to see the pattern on the packaging or personal care article. However, from the standpoint of older users, the size of the pattern may have to be increased beyond that which is shown in FIG. 14, in order for the pattern to be visible.

Another factor to consider in selection of color and a pattern is the contrast limits between the pattern and the adjacent surroundings. If the contrast is not sufficient, then the pattern may not be viewable, even if it is with the size requirements shown in FIG. 14. Generally, the contrast needs to be at least 0.05 on a scale of 0 to 1 in order for a pattern to be visible. 0 is no contrast and 1 is maximum contrast.

Patterns can be more discrete if the pattern is less linear and less perpendicular. In current package and personal care article configurations. Generally, when it comes to incontinence pad and liners and feminine care pads and liners, the silhouettes of or marking on the pads or liners may be visible through the packaging. To make the silhouette and marking more discrete, patterns could be placed on the packaging component in the regions where the pad or liners are visible through the packaging or patterns could be placed on the pad or liner to help hide the silhouette of the pad or liner. By having the pattern on the personal care article being the same as the pattern of the patterns on the pad or liner tends to blend in with pattern on the packaging component.

Another way to coordinate the article component and the packaging component is to provide a common shape (other than a straight line) to both the article and the packaging component. While absorbent articles have shapes which make them useful for their intended purpose, some components or aspect of the absorbent article have shapes which can be varied without determent to the functionality of the absorbent article. For example, the peel strip that protects the garment adhesive may have shapes at the end which are scalloped, sine wave or any other shape. Likewise, the side edges of the peel strip may also be shaped. Another element of the absorbent component such as the surge layer or tissue layer which is positioned between the absorbent core and the body side liner. The surge layer or tissue layer may also be shaped with a similar shape as the peel strip described above. It is noted that only one of the peel strip or surge/tissue layer needs to be shaped in order to coordinate with the packaging component. On the packaging component, especially the end of the second panel on the pouch, the sides of the pouch, or the ends or sides of the wrapper may also be shaped with the same shape with identical dimensions or which is proportional to the dimensions of the shape of the peel strip and/or distribution layer/tissue layer. Other elements of the absorbent component or the packaging component may be similar shapes, provided that the functionality of the absorbent article or packaging component is not compromised. In addition, shaping the peel strip and or end of the second panel of the wrapper component may have additional benefits of aiding the user in locating the peel strip or opening of the packaging component.

In another aspect of the present invention, the wrapper component is does not have any visual characteristics that are coordinated thereon. However, the wrapper component appears to be coordinated and matched to the absorbent article. In this aspect of the present invention, the wrapper component is clear or translucent, such that the visual characteristics on the absorbent article are visible through the wrapper component. In the case of color as the visual characteristic, and with a translucent wrapper component, the hue of the visible color will be the same but the saturation and luminosity will be different.

In some embodiments, the article and packaging components can also be coordinated by other sensory characteristics, for example touch and smell. For example, the packaging component can have the same texture as the article component, so as to provide a coordinated tactile characteristic. In some embodiments, the tactile characteristic is formed by an embossment, or different embossments. Similarly, separate pieces of the same type of material may be applied to the article and packaging components.

By coordinating the packaging component and the personal care articles, many benefits may be obtained. First, the coordination allows for thinner and cheaper wrapper/packaging components to be used. When the personal care article and the wrapper/packaging have the same color or pattern, especially on the garment side outer cover and/or peel strip, and the same color or pattern is on the wrapper/packaging, it is more difficult to discern what the contents of the wrapper are. Therefore, coordination of the wrapper/packaging with the personal care article helps disguise the personal care article in the thinner wrapper/packaging component. Second, the coordination of the wrapper/packaging with the personal care article may provide an emotional benefit to the user and allow the products to fit into a user's life. Items which appear to be designed together makes the user more confident in using the products since the coordination makes the overall product of higher quality as compared to uncoordinated products.

In another embodiment of the present invention, the visual characteristics may be connected to other senses, such as smell and feel. That is, the color or pattern may contain a floral color or a floral pattern. A scent can associated with the color or pattern may be applied to the article or packaging. For example, a purple color or a pattern of lavender flowers could be associated with a lavender scent.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A visually coordinated absorbent product comprising:
   an absorbent article component comprising a body side liner, a garment side outer cover and an absorbent core disposed between said body side liner and said garment side outer cover;
   a first packaging component having at least first and second visual characteristics, wherein said article component is disposed in said first packaging component; and
   a second packaging component having said at least said first and second visual characteristics, wherein said first packaging component is disposed in said second packaging component.

2. A visually coordinated absorbent product comprising
   an absorbent article component comprising a garment side outer cover and an absorbent core adjacent said garment side outer cover, wherein said article component has at least a first and second visual characteristic, wherein said first visual characteristic is different than said second visual characteristic; and
   a packaging component which is transparent or translucent and the a first and second visual characteristics are visible thru the packaging components such that the packaging component appears to have the a first and second visual characteristics on the surface thereof.

* * * * *